(12) United States Patent
Seymour et al.

(10) Patent No.: US 8,941,390 B2
(45) Date of Patent: Jan. 27, 2015

(54) SYSTEM AND METHOD FOR TESTING ELECTRICAL CIRCUITS USING A PHOTOELECTROCHEMICAL EFFECT

(71) Applicant: NeuroNexus Technologies, Inc., Clarence, NY (US)

(72) Inventors: John P. Seymour, Ann Arbor, MI (US); Abeer Khurram, Ypsilanti, MI (US)

(73) Assignee: NeuroNexus Technologies, Inc., Ann Arbor, MI (US)

( * ) Notice: Subject to any disclaimer, the term of this patent is extended or adjusted under 35 U.S.C. 154(b) by 218 days.

(21) Appl. No.: 13/781,809

(22) Filed: Mar. 1, 2013

(65) Prior Publication Data

US 2013/0229188 A1 Sep. 5, 2013

Related U.S. Application Data

(60) Provisional application No. 61/759,608, filed on Feb. 1, 2013, provisional application No. 61/605,488, filed on Mar. 1, 2012.

(51) Int. Cl.
*G01R 27/28* (2006.01)
*G01R 31/02* (2006.01)
*G01R 1/067* (2006.01)

(52) U.S. Cl.
CPC .......... *G01R 31/026* (2013.01); *G01R 1/06783* (2013.01)
USPC ................ 324/660; 324/501; 257/88; 257/98

(58) Field of Classification Search
USPC ............... 324/754.01–754.29, 329, 501, 648, 324/660, 71.5; 257/88, 98
See application file for complete search history.

(56) References Cited

U.S. PATENT DOCUMENTS

| | | | |
|---|---|---|---|
| 4,473,795 A | | 9/1984 | Wood |
| 5,760,597 A | * | 6/1998 | Yoshida et al. .......... 324/754.23 |

(Continued)

FOREIGN PATENT DOCUMENTS

| | | |
|---|---|---|
| EP | 2634588 EP | 10/2014 |
| FR | 2957703 | 8/2009 |

OTHER PUBLICATIONS

"EP Search", 13157400.6, Sep. 23, 2014.

(Continued)

*Primary Examiner* — Tung X Nguyen
*Assistant Examiner* — Alesa Allgood
(74) *Attorney, Agent, or Firm* — Michael F. Scalise

(57) ABSTRACT

A test system for medical devices that does not require physical contact with an electrical site along a conductive path is described. Not having to physical contact an electrical site while performing an electrical continuity test avoids potential damage to the site. The test system includes a fluidic channel that dispenses an electrolytic solution onto a first electrical site on the conductive path. A light source irradiates the first site to thereby induce a photoelectrochemical (PEC) effect at an interface thereof. The PEC effect produces a change in both the potential (i.e., voltage) and current carrying ability in the conductive path. That voltage or current is measured at a second site to determine whether there is electrical continuity or discontinuity between the sites on the conductive path.

21 Claims, 21 Drawing Sheets

(56) References Cited

U.S. PATENT DOCUMENTS

| | | | |
|---|---|---|---|
| 6,369,591 B1* | 4/2002 | Cugini et al. | 324/750.14 |
| 6,452,410 B1 | 9/2002 | Parker | |
| 7,112,967 B2* | 9/2006 | Tsuji et al. | 324/501 |
| 2002/0113598 A1 | 8/2002 | Tsuji et al. | |
| 2005/0258816 A1* | 11/2005 | Zen et al. | 324/96 |
| 2006/0139040 A1 | 6/2006 | Nystrom et al. | |
| 2006/0139041 A1 | 6/2006 | Nystrom et al. | |
| 2009/0294305 A1* | 12/2009 | Bekki et al. | 205/792 |
| 2010/0200431 A1* | 8/2010 | Kim et al. | 205/791 |
| 2012/0070922 A1* | 3/2012 | Yang et al. | 438/27 |

OTHER PUBLICATIONS

Abeer Khurram and John P. Seymour, "Investigation of the photoelectrochemical effect in optoelectrodes and potential uses for implantable electrode characterization", 35th Annual International Conference of the IEEE EMBS, Osaka, Japan, Jul. 3-7, 2013.

Kenichi Honda, Dawn of the evolution of photoelectrochemistry, Journal of Photochemistry and Photobiology A: Chemistry 166 (2004) 63-68.

* cited by examiner

Galvanostat

Potentiostat

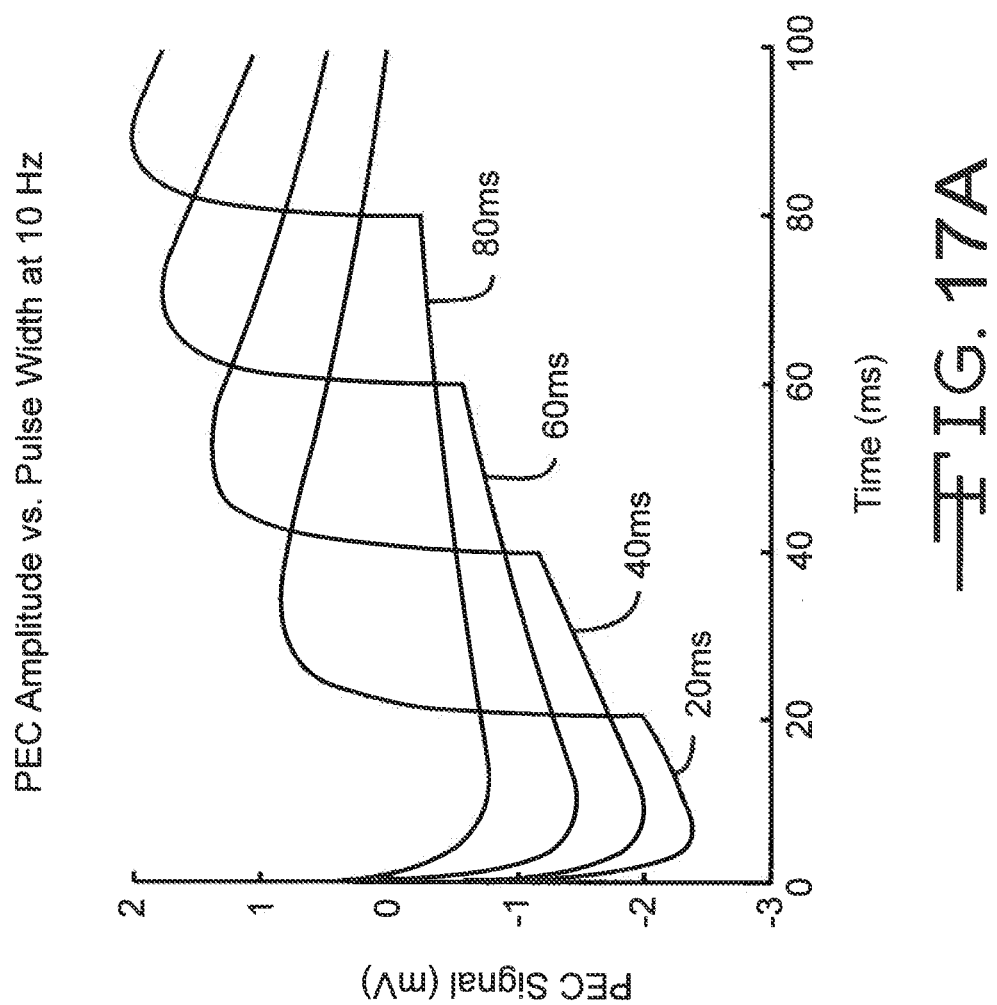

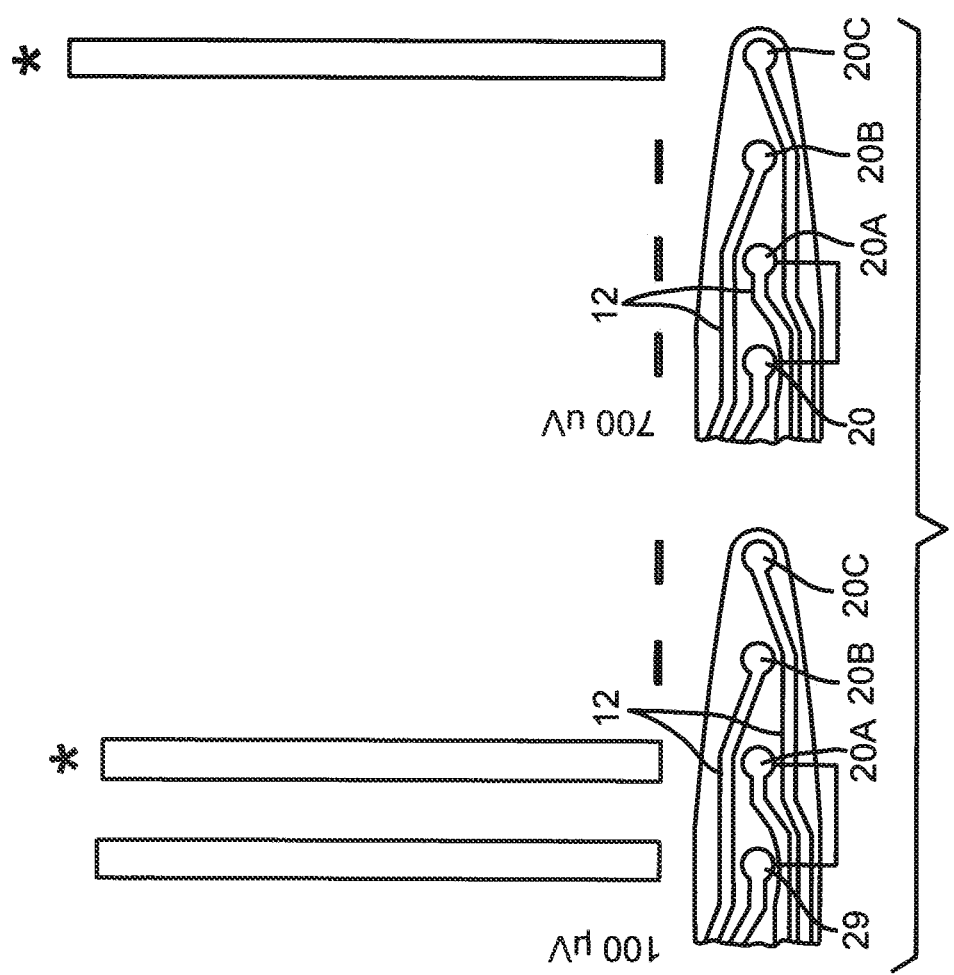
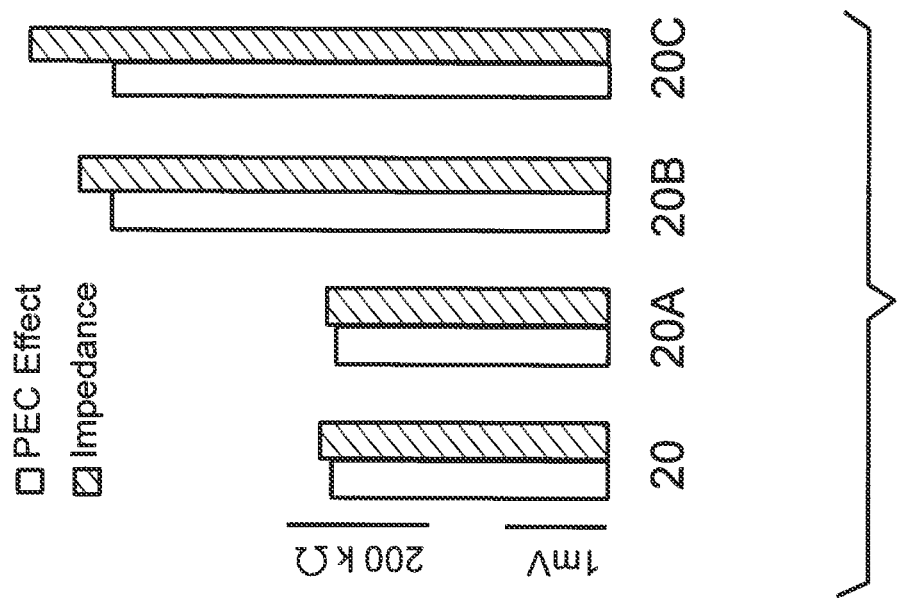
FIG. 19A
FIG. 19B

US 8,941,390 B2

SYSTEM AND METHOD FOR TESTING ELECTRICAL CIRCUITS USING A PHOTOELECTROCHEMICAL EFFECT

CROSS-REFERENCE TO RELATED APPLICATIONS

This application claims priority from U.S. provisional patent application Ser. Nos. 61/605,488, filed on Mar. 1, 2012 and 61/759,608, filed on Feb. 1, 2013.

BACKGROUND OF THE INVENTION

1. Field of the Invention

This invention relates generally to the electronic device testing applications, and more specifically to a new and useful system and method for testing electrical circuits using a photoelectrochemical effect. Electronic device testing also includes medical device electrodes, microelectrodes, and nanoelectrodes.

2. Prior Art

A device with electrical traces or other electrically conductive paths, such as a medical device with electrode sites for stimulation and/or recording, typically requires one or more manufacturing tests to verify electrical continuity or impedance equivalent within the traces. These tests detect defects, such as unwanted open-circuits (breaks), high resistance, or short-circuits, within the conductive paths. Electrical continuity or impedance equivalent measurement in any passive electrical device requires contacting electrical pads. Depending on intent, a contact pad is variously known as a bond pad, terminal, test pad, via, or electrode. Conventional electrical continuity tests generally require two physical contacts to create an anode and cathode. For example when testing a medical device, a first physical contact may be the electrode site on the medical device, and a second one is on a proximal portion (e.g., bond pad) of the medical device.

However, many devices have relatively small dimensions that make physical contact with specific electrode sites or contact pads difficult and potentially damaging. In particular, medical and chemical sensors with electrode sites having diameters below approximately 100 µm risk damage as a result of physical contact with the sites during electrical continuity tests. Some microelectrodes, for example those that are typically used for sensing can be as small as 5 µm in diameter. Conventional electrical probe equipment (e.g., wire probes, MEMS probes, vertical probes) are generally not small enough to provide a reliable means of testing without damaging the microelectrodes.

Another method for electrical testing of an electrode or microelectrode is to submerge the electrode in an electrolyte and conduct an impedance measurement. The electrolyte must be of sufficiently low resistance to allow current to flow through the solution and back to a counter electrode. This technique applies a signal from the measurement tool to the circuit and requires very sensitive electronics and low capacitance leads to improve its dynamic range. Commercial impedance measurement devices also take two to twelve seconds for a single frequency measurement of 1,000 Hz (lower frequencies take longer). For commercial applications, that amount of time can be cost prohibitive.

Thus, there is a need in electronic testing field to create a new and useful system for testing electrical continuity or impedance equivalent between two physical contacts of a medical device, and the like. Moreover, the new test system and method must minimize risk to the structure of the physical contacts. Conventional neuromodulation devices have increasing electrode counts. In fact, thin-film MEMS-based devices may have hundreds of electrodes. A single wafer may contain 20,000 to 100,000 microelectrodes.

What is, therefore, needed is a reliable system for automated testing of thousands of devices on a wafer. The new test system must be especially sensitive to defects like opens and short-circuits. There is also a need to test small electrical contacts in integrated circuits without the expense of wire cantilever or MEMS-based cantilevers, commonly called "probes" in the electronics industry. MEMS cantilever devices are currently capable of probing 45-micron square bond pads with a minimum scrub length (sliding contact distance) of 15 microns. In that respect, the test system of the present invention has been used with sub-micron diameter contacts and been shown to provide relatively large amplitude signals. Such signals are reliably useful as a novel alternative to current testing methods.

BRIEF DESCRIPTION OF THE FIGURES

FIGS. 17A to 17C are graphs constructed from the sensitivity of the PEC amplitude to light pulses of 10 Hz, 50 Hz and 100 Hz, respectively, and at duty cycle of 20%, 40%, 60% and 80% at each frequency.

FIGS. 19A and 19B show use of the PEC effect in short-circuit detection and illustrates the advantage this invention has over impedance measurements to detect short circuits.

DESCRIPTION OF THE PREFERRED EMBODIMENTS

As used herein, the term electrolyte refers to a conducting medium in which the flow of current is accompanied by the movement of matter in the form of ions. That is regardless whether the electrolyte is a liquid electrolyte that is relatively flowable or of a gel-like film that is relatively viscous.

Figure 1:
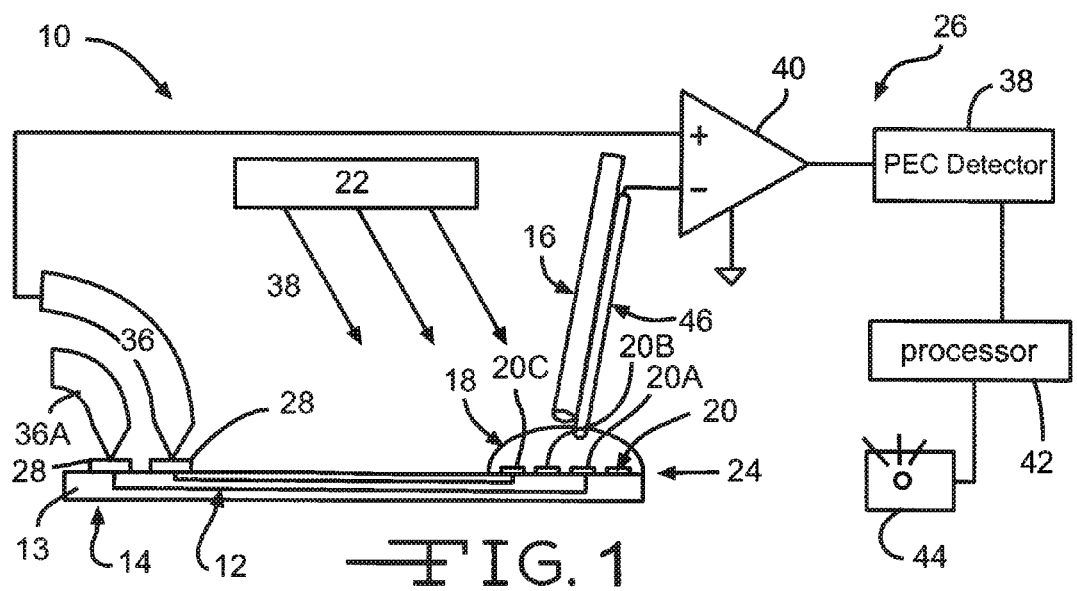
FIGS. 1 and 2 are schematics of the system of the present invention.
Figure 2:
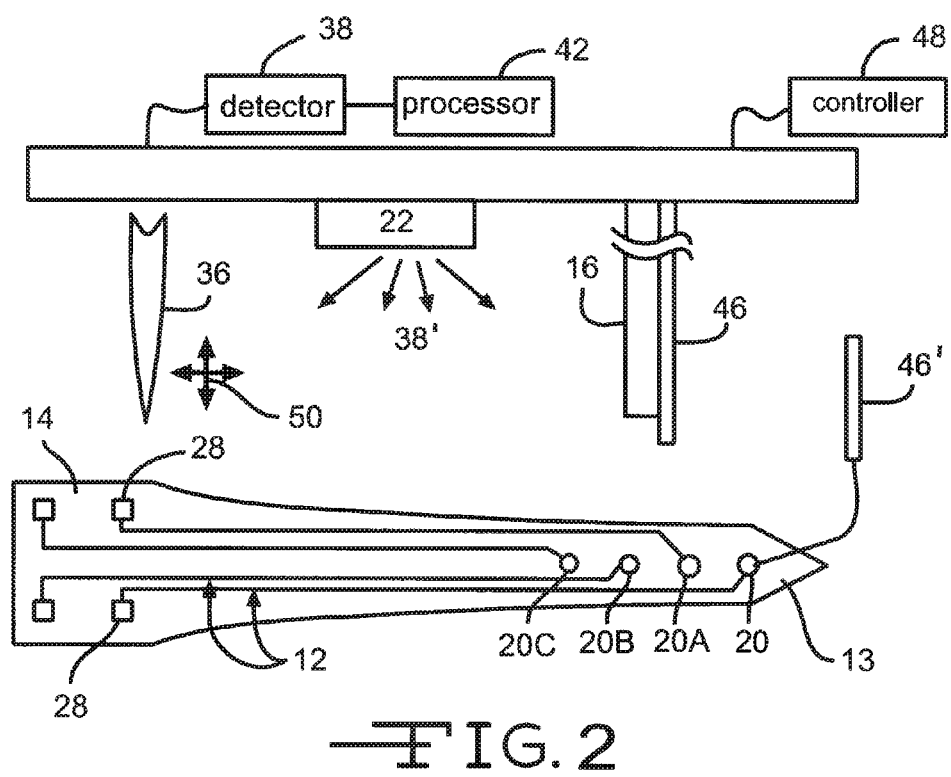

Turning now to the drawings, FIGS. 1 and 2 illustrate a system 10 for testing the electrical continuity or impedance equivalent of a conductive trace or path 12 of an electronic device 14. The conductive trace is supported on a substrate 13 of an electrically insulative material.

The test system 10 optionally includes a fluidic channel 16 configured to dispense an electrolytic solution 18 to a first point or site 20 on the conductive path 12. As an alternative to a fluidic channel, the electrolyte may be patterned using a direct-write print head or patterned using other lithography techniques. A light source 22 is configured to irradiate the first site 20. The irradiation induces a photoelectrochemical (PEC) effect at an interface 24 between the irradiated site 20 on the conductive path 12 and the electrolytic solution 18. A detection system 130 is configured to detect and measure at least one of a voltage or a current at a second site 28 on the conductive path 12. The respective sites are spaced sufficiently far apart from each other so that illumination of the first site 20 does not cause an appreciable PEC effect at the second site 28.

The PEC effect at the interface 24 between the irradiated site 20 on the conductive path 12 and the electrolytic solution 18 produces a change in both the potential (i.e., voltage) and current in the unbroken conductive path 12. Then, measuring the voltage and/or current in the closed circuit by contacting the second site 28 is used to determine whether there is electrical continuity or discontinuity between the first site 20 (where the PEG effect is induced) and the second site 28 on the conductive path 12.

Figure 12:
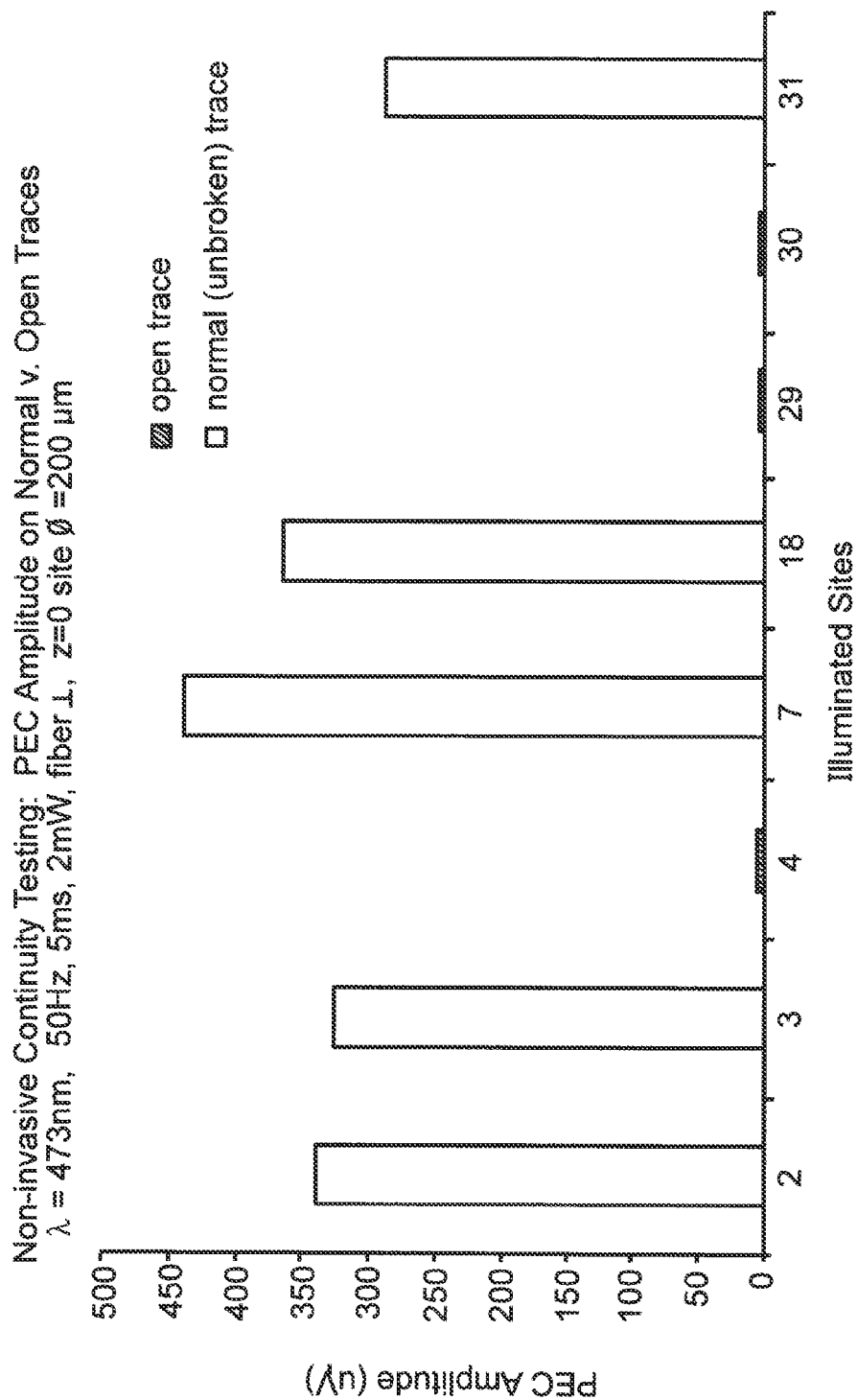
FIG. 12 is a chart of non-invasive continuity tests of PEG amplitude depicting a normal or unbroken circuit trace in comparison to an open trace.

As shown in FIG. 12, in an electronic device 14 in which the conductive path 12 is unbroken, the measured voltage and/or current is a result of the PEG effect induced between the electrical sites 20 and 28. The measured voltage or current is significantly higher than that measured in a device in which the conductive path 12 is open or broken.

As shown in FIGS. 1 and 2, in a preferred embodiment, the test system 10 is configured to test electrical continuity or impedance equivalent in a medical device 14, particularly along conductive traces or other paths passing from the first electrode or site 20 to the second, spaced apart or distant electrode or site 28. Any material that readily passes an electrical current is considered to fall within the definition of an electrical path, trace or site, including an electrical contact, bond pad, medical electrode, and the like. The second electrical site 28 must also be physically capable of contact with an electrical probe while the spaced apart first electrical site 20 is in contact with the electrolyte. In this embodiment, the test system 10 preferably induces the PEG effect on an electrode site and measures the voltage and/or current at a location along the corresponding conductive trace and/or at a bond pad that is intended to be in electrical communication with the first site.

Alternatively, the test system 10 can induce the PEG effect and measure voltage and/or current at first and second spaced apart points or sites 20, 28 that are not intended to be in electrical communication or continuity with each other, such as to verify a desired open circuit. The sites 20, 28 are preferably conductive and include a metal, a metal oxide, doped diamond, graphite, carbon nanofiber, and/or a conductive polymer, but can include any suitable material that enables inducement of the PEC effect at the site.

In that respect, the system 10 provides an electrical test for an electrical device, such as a medical device, without directly contacting at least one of the spaced apart electrical sites 20, 28, thereby avoiding potential damage to the uncontacted site. The test system 10 preferably provides a quick, reliable way to verify electrical continuity or flag undesirable electrical discontinuity in an electronic device 14. However, the test system 10 can additionally or alternatively verify desired electrical discontinuity (e.g., check for mutually exclusive conductive traces intended to carry different electrical signals) in an electronic device 14. The test system 10 preferably reduces overall component cost and time for manufacture since the system does not require probes or pads that are specifically designed for the particular device being tested. Moreover, the test system 10 can be scaled according to varying manufacturing needs and requirements. The test system 10 can be configured to test individual devices, one at a time, or a plurality of devices arranged either in series or parallel, for example multiple devices aligned together side-by-side on an insulative wafer or other thin-film insulative substrate.

For clarity, the system 10 is primarily described herein in reference to the first site 20 on the conductive path 12 (where the PEC effect is induced) being a distal electrode on a medical device 14, and the second site 28 where the voltage and/or current is measured being a test pad or bond pad at a proximal end of the medical device. However, it should be understood that the system 10 can be configured to test for continuity or discontinuity between any two suitable sites on a conductive path 12 of a medical device or any other suitable electronic device.

Figure 3A:
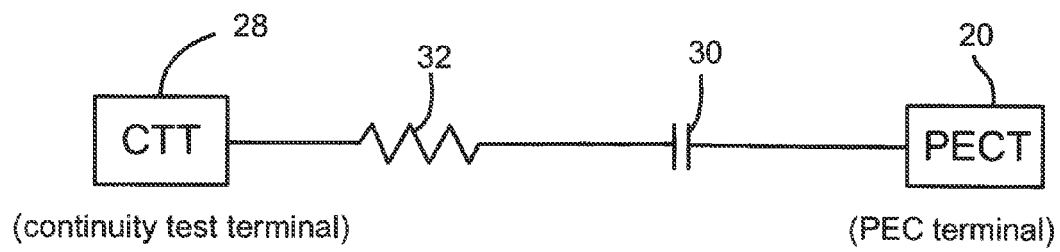
FIGS. 3A and 3B are schematics of exemplary medical electrode devices suitable for use with the system of the present invention.

The first site 20 can be any metal surface with a conductive trace connecting it directly or indirectly through other electrical components (resistors, capacitors, inductors, or even active components) to the test pad 28. For example, the medical device 14 can include one or more passive circuits 30 and 32 (FIG. 3A) or an active circuit 34 (FIG. 35) in the conductive path between the first and second sites 20, 28.

The photoelectrochemical effect occurs at the interface between many metallic compounds and an ionically conductive solution. Gold, platinum, iridium, tungsten, platinum-iridium alloys, poly(3,4-ethylenedioxythiophene) or (PEDOT), iridium oxide, and many other metals have varying amplitudes of the photoelectrochemical artifact. However, U.S. Patent Application Pub. No. 2011/0087126 to Zorzos et al. teaches that indium tin oxide (ITO) does not respond with a photoelectrochemical effect. Regardless, most metals create peak-to-peak potential that is higher than the electronic and thermal noise measured with a typical high-impedance amplifier.

Figure 16A:
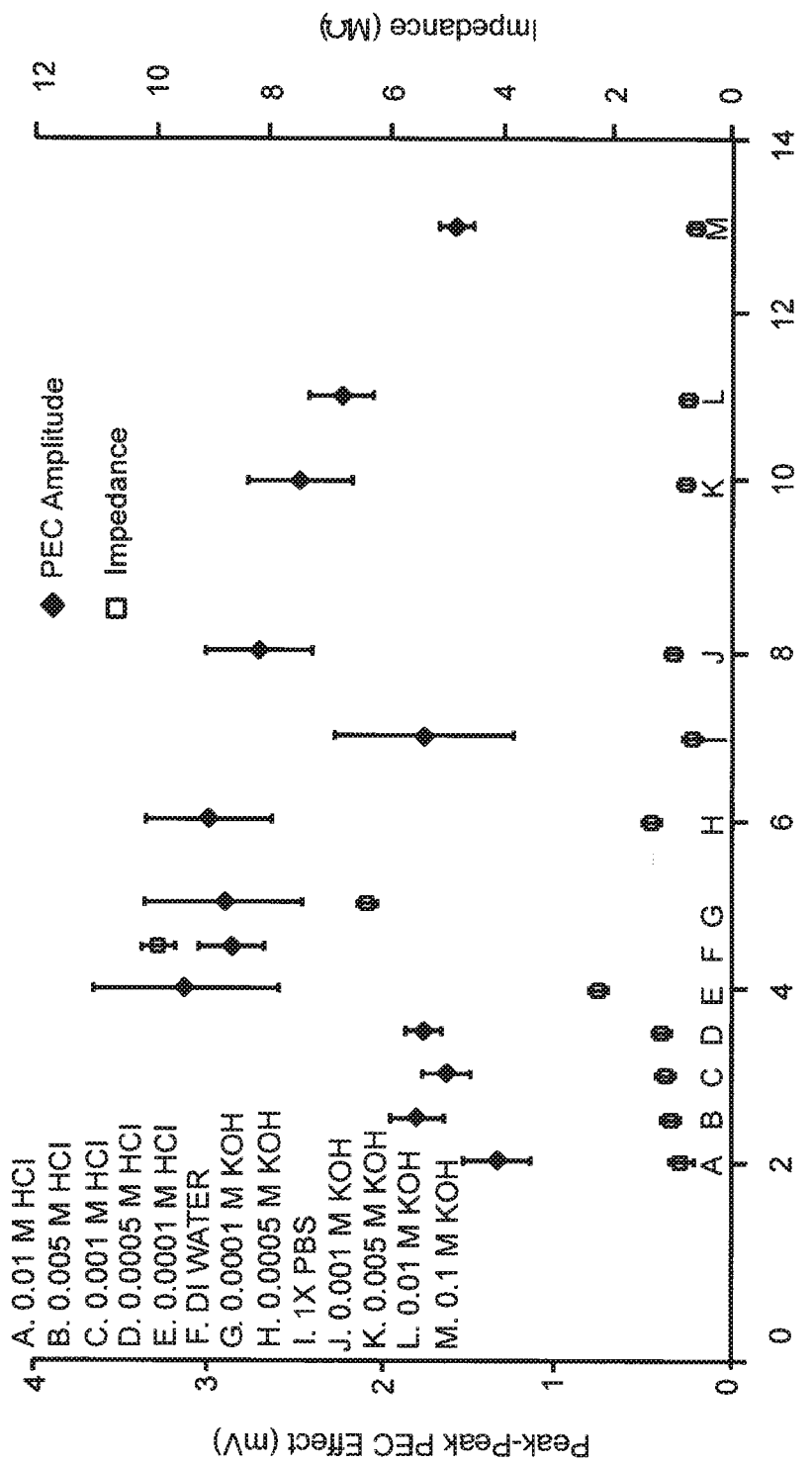
FIG. 16A is a chart comparing the sensitivity of impedance measurements and PEG amplitude as a function of pH.
Figure 16B:
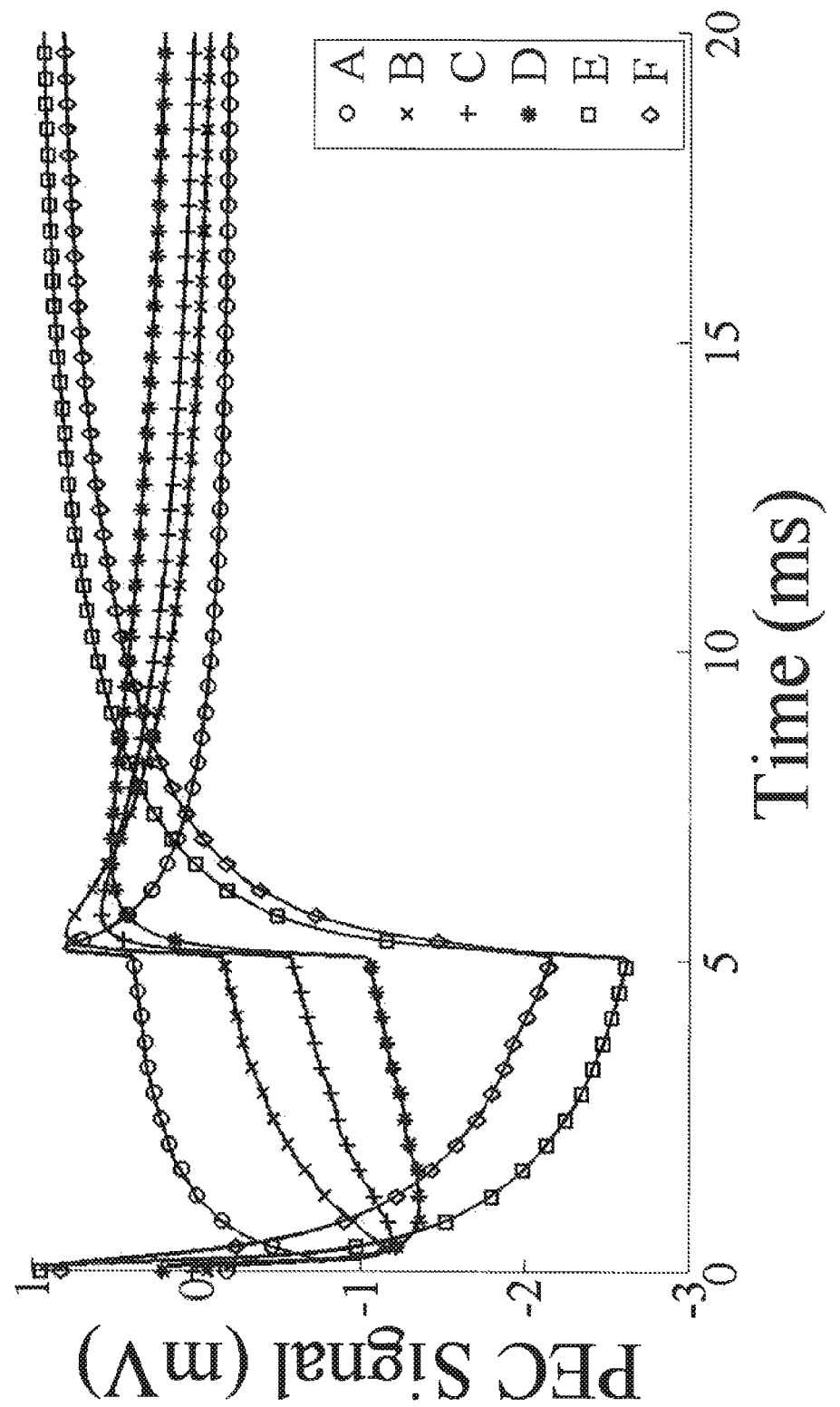
FIGS. 16B and 16G are graphs constructed from the PEG amplitude as a function of pH for the respective electrolytes listed in FIG. 16A.
Figure 16C:
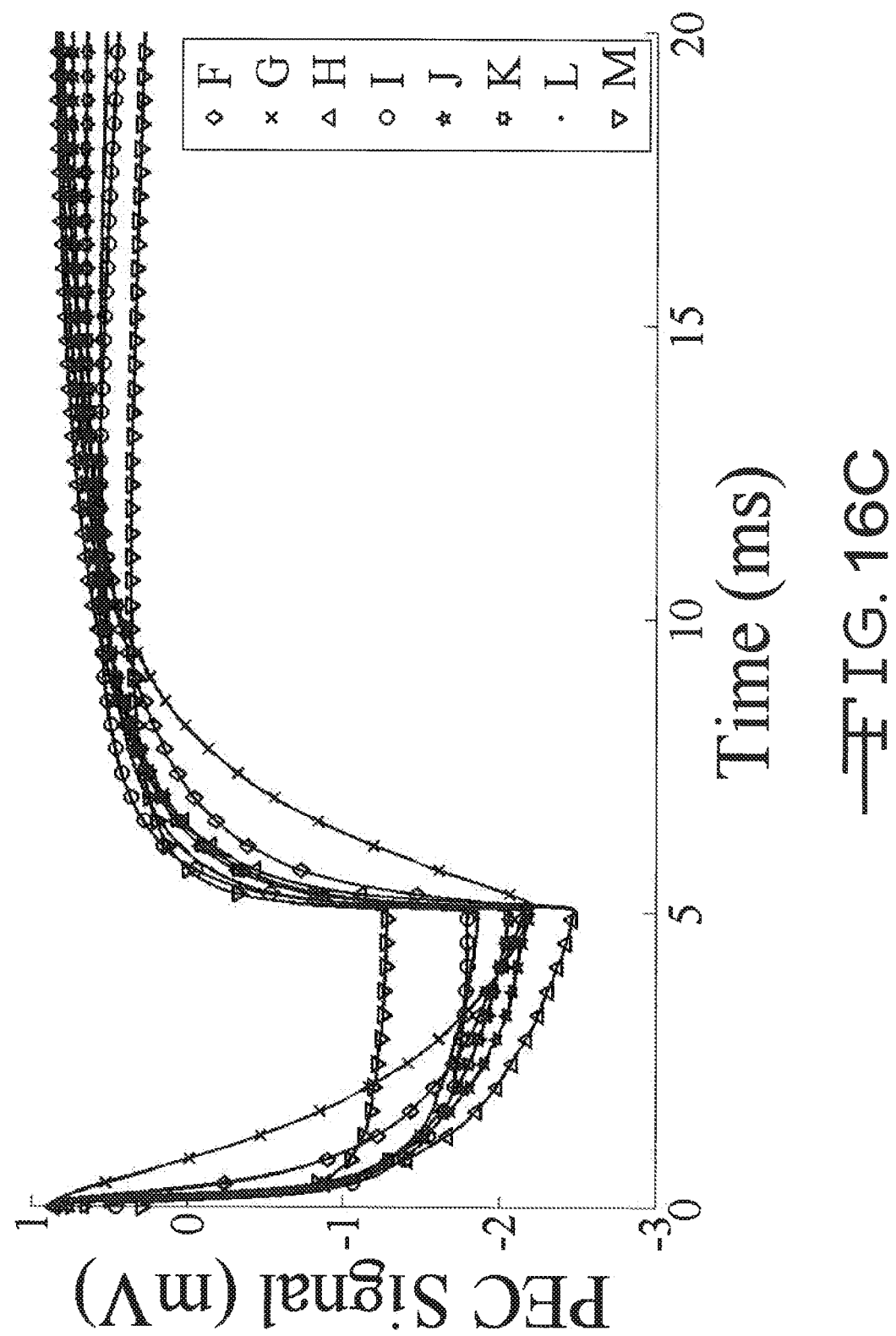

The electrolyte 18 can be a buffered solution of ions. It can also be a simple acid or base. According to the present invention, a wide range of pH values is effective (FIGS. 16A to 16C) at generating a relatively large signal response. Suitable electrolytes include HCl ranging from about 0.01M to about 0.005M, KOH ranging from about 0.0001M to about 0.1M, deionized water, phosphorous buffered saline (PBS), and mixtures thereof. The exemplary electrolyte solutions listed in FIG. 16A are designated electrolytes A to M. A preferred electrolyte is of a relatively low concentration base, e.g. 0.0005 M KOH (electrolyte H in FIGS. 16A and 16C). This electrolyte has been shown to create a large amplitude response and remain relatively stable for small concentration changes. Moreover, the PEC effect is sensitive to the species present in an electrolyte. This is shown by the different voltage responses for the acidic electrolytes graphed in FIG. 16B and the basic electrolytes graphed in FIG. 16C.

It is preferred that the electrolyte 18 be patterned on the electrical site 20 using a fluidic delivery system or print technology (e.g. inkjet) or be applied as a gel-like film and then patterned. A commercially available inkjet pattern generator, having controllable dot size and volume size, is preferred. Inkjet pattern generators usually have software that reads in a computer-assisted-design file (CAD) which instructs the tool where to dispense the inking medium. The surface tension of the ink medium effects viscosity that is an important dispensing factor, but must be high enough to ensure the inked electrolyte 18 does not readily evaporate after being dispensed. If testing requires many thousands of PEC measurements which take on the order of one second per measurement, for example, then the inking medium should be engineered such that there is little evaporation and, therefore, only small changes in the electrolyte conductivity over the course of the test, which in this example could take several hours.

As commonly reported, the addition of most inorganic salts will increase surface tension. That is in addition to or independent of other ionic additions. For example, a small concentration of NaCl may replace or supplement a small concentration of KOH. Additionally, the use of a gelatinous additive (added to the original solution or dispensed separately) will also help reduce evaporation. Examples of a useful gel include PEG (or polyethylene glycol), glycerine, and other polymers like CMC (carboxymethylcellulose), which all increase the viscosity of the medium and decrease the evaporation rate.

Another advantage to use of an inkjet pattern generator is that the second electrical site 28 needs to be dry and in direct contact with an electronic probe 36. Suitable direct contact probes are, for example, conventional cantilever probes, MEMS-based probes, or vertical probes. Each of these are manufactured in slightly different ways and have trade-offs in terms of contact size, scrub-in length, precision, lifetime, and cost.

Another cost advantage for the proposed PEC measurement system over conventional direct contact methods includes the fact that tooling costs for a given setup can be reduced. Conventionally, if either the anode or cathode contact (first and second sites 20, 28) pad is moved, then the probe array must also be modified to match the new pad location. In the present invention, the direct contact sites may be kept in a fixed location and the first micro-contact site 20 may be moved without new tooling costs. Illumination of the first site 20 may be directed at the new location by programming a laser or broadband light source to move to that new location. Alternatively, illumination may be directed broadly as well, although this is less effective for detecting short circuits. The electrolyte pattern 18 does not need to change assuming that the electrolyte patterns everything except the second contact site 28.

In one embodiment, the fluidic channel 16 is used to dispense an electrolyte 18 on the first electrical site 20 along the conductive path 12. That forms the electrode-electrolyte interface 24. Alternatively, the fluidic channel 16 is configured to dispense an electrolyte 18 on each of a plurality of electrical sites 20A, 20B and 20C, etc. For instance, the fluidic channel 16 can be physically moved between electrical sites 20 and 20A to 200 in series. Alternatively, the medical device 14 is moved to serially align each of its multiple electrical sites 20 and 20A to 20C with the fluidic channel 16. In another embodiment, the test system 10 preferably includes multiple fluidic channels 16 that are configured to deposit an electrolyte 18 on multiple electrical sites 20 and 20A to 20C in parallel.

The fluidic channel 16 is preferably a microfluidic tube or other channel having a lumen that is configured to carry the electrolyte 18. In one embodiment, the fluidic channel 16 is couplable to an external supply of the electrolyte 18. In another embodiment, the fluidic channel 16 is a vessel filled with the electrolyte 18 independent of an external fluidic supply. The fluidic channel 16 can include valves or other suitable control mechanisms to regulate the amount of electrolyte that is applied to the electrode site 20. In a preferred embodiment, the fluidic channel 16 is configured to deposit approximately a few nanoliters of electrolyte 18 onto the electrode site 20. Alternatively, the fluidic channel 16 is configured to deposit any suitable amount of electrolyte 18 onto any desired location along the conductive path 12, depending on the application of the test system 10. When used in this way, the counter electrode 46 may be moved into proximity with the electrical site 20 under test to ensure a closed-loop circuit is formed.

Figure 4:
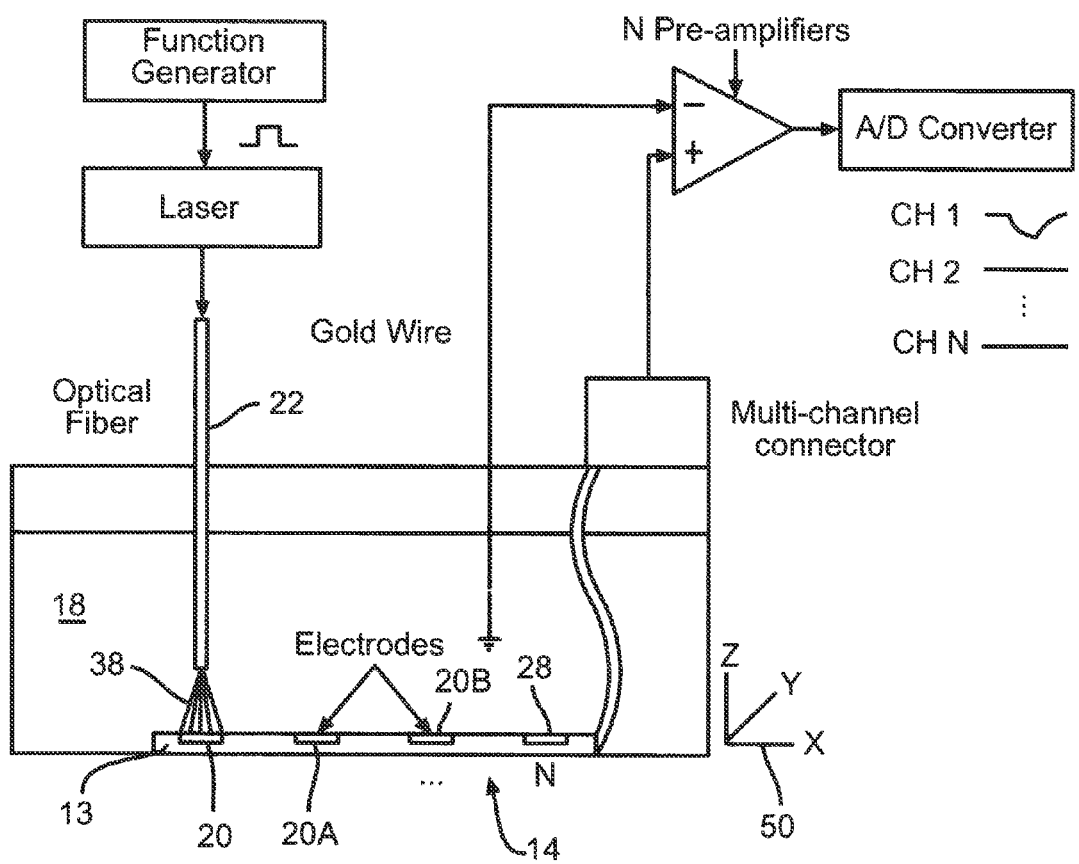
FIG. 4 is a schematic of one preferred embodiment of the present invention submerged in an electrolyte.

As shown in FIG. 4, in another embodiment, the electrolyte 18 may be a fluid bath immersing the entire device 14 including the first and second electrical sites 20, 28. This technique is appropriate where the device 14 under test is assembled to a sealed electrical interface. Instances of this technique may include wire bonding, ball bonding, soldering, etc, the conductive trace or path 12 to a printed circuit board that is coated in with a water-resistant insulator.

Figure 11:
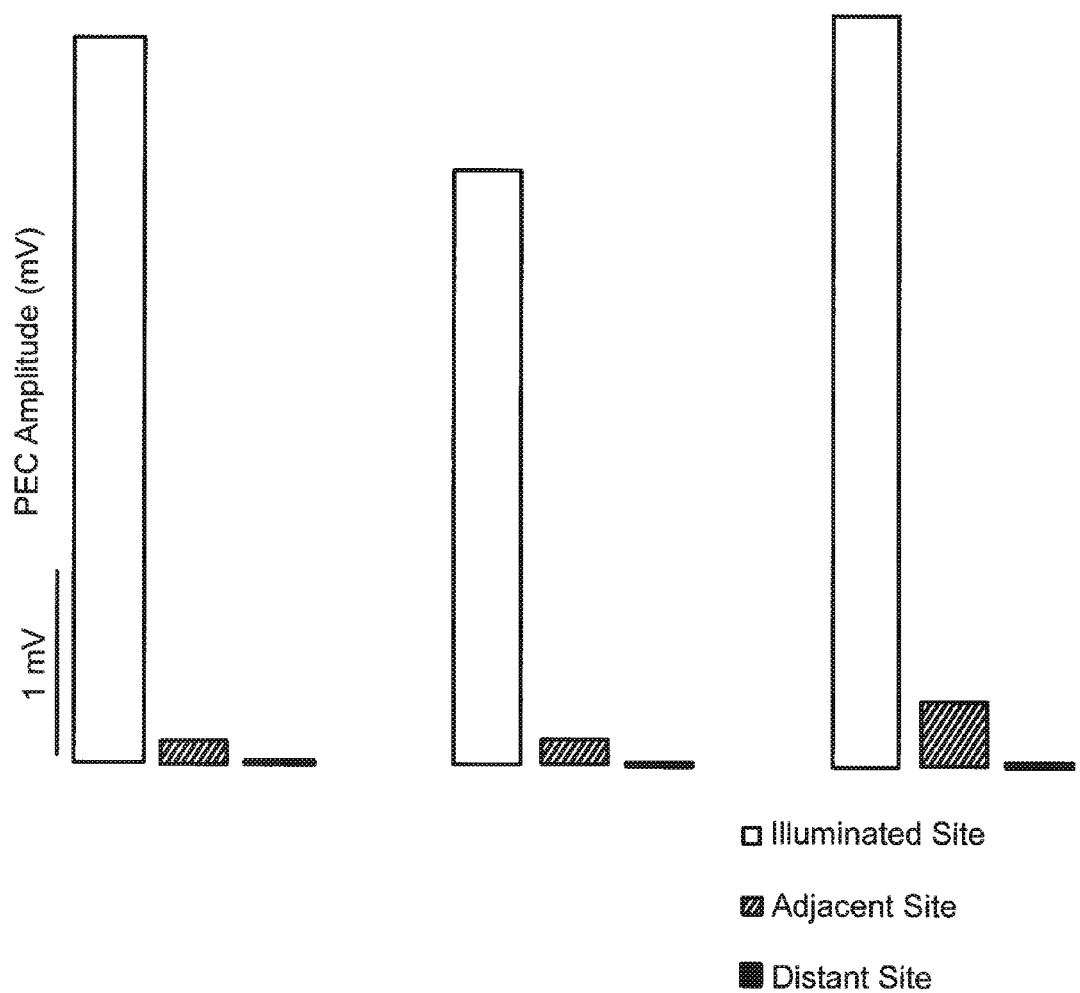
FIG. 11 is data gathered from an example implementation of the system and method of the present invention.

The light source 22 serves to induce a photoelectrochemical (PEC) effect on at least the first electrode site 20 on the conductive path 12. That is by irradiating the electrode site 20 to induce a PEC effect at the irradiated electrode/electrolyte interface 24. As shown in FIG. 1, the light source 22 is configured to focus its luminescent radiation 38 onto a plurality of serially arranged electrical sites 20 and 20A to 20C, one at a time. The light source 22 can be physically moved from one electrode site 20 and 20A to 20C to the next to thereby irradiate each of them in series, and/or the medical device 14 can be physically moved to serially align each of the electrical sites 20 and 20A to 20C with the light source 22. The focused irradiation 38 preferably produces a localized PEG effect. In some applications the localized PEC effect can be used to test for interactions with nearby circuitry such as cross-talk or interference between multiple conductive paths (FIG. 11). In a second embodiment shown in FIG. 2, the light source 22 produces a multi-directionally emitted light radiation 38 that simultaneously irradiates two or more electrode sites 20 and 20A to 20C in parallel. A preference between using focused irradiation 38 and a multi-directionally emitted light radiation 38' depends on a particular application, such as sensitivity of the medical device 14 to the photoelectric effect.

The photoelectric effect is an entirely different phenomenon than the photoelectrochemical effect. A practical issue is whether the photoelectric effect is likely to cause undesirable false positives and/or false negatives during testing. If the device under testing is susceptible to the photoelectric effect, then using a broadly directed light source is undesirable since an electrically discontinuous conductive path 12 as an open circuit can still have a photoelectrical response that results in a "false negative" for electrical continuity or impedance equivalent. In that respect, the light source 22 is configured to irradiate at least the electrode site 20 with a desired light intensity.

Figure 14:
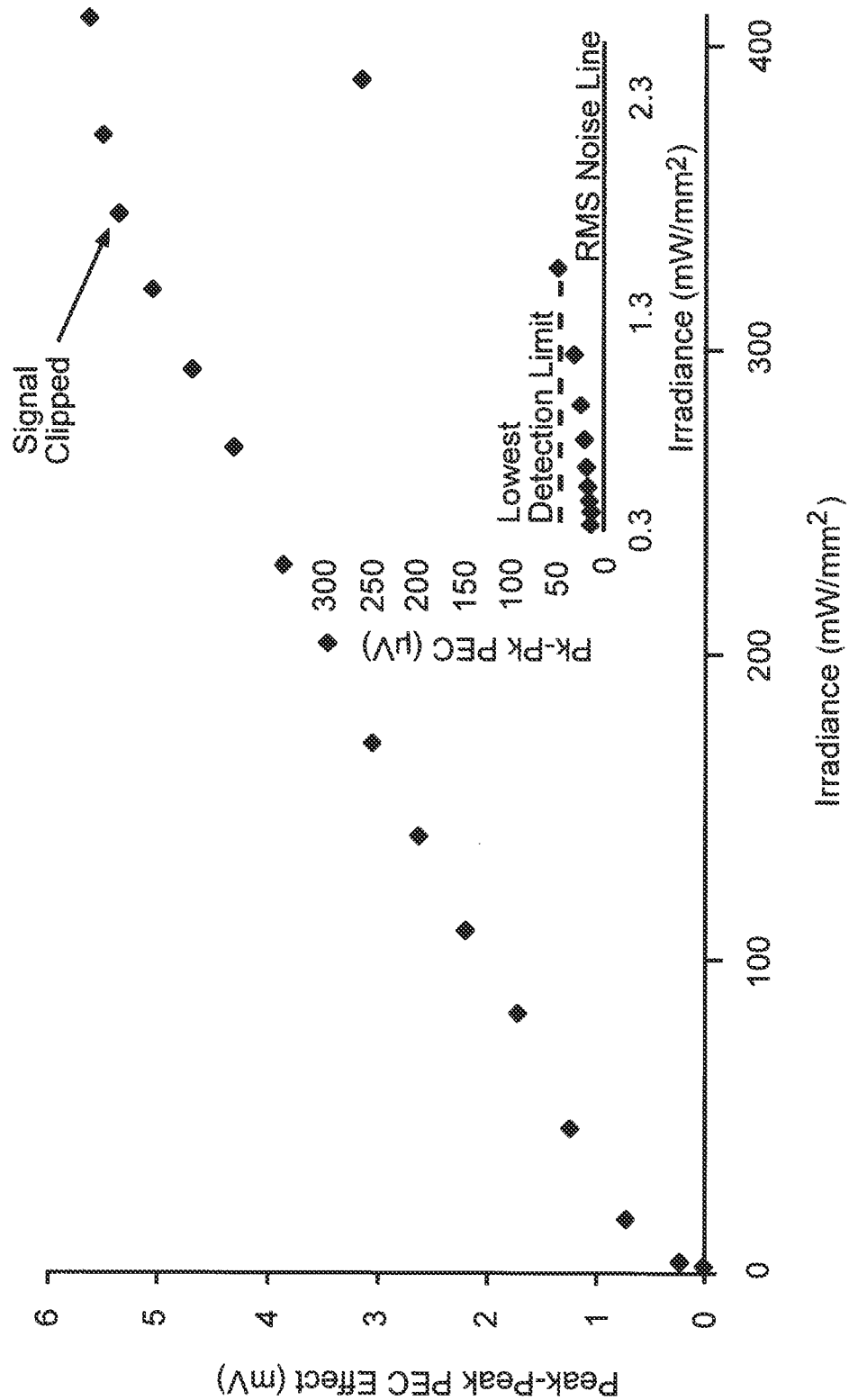
FIG. 14 is a chart of PEG amplitude for varying irradiance.

As shown in FIG. 14, the PEC effect indicated by the amplitude of the voltage measured at an exemplary second site 28 on a conductive path 12 is approximately linear and proportionally related to the intensity of the applied light for a broad span of power. Of course, sensitivity of the response depends in part on the sensitivity of the detection electronics.

Figure 20:
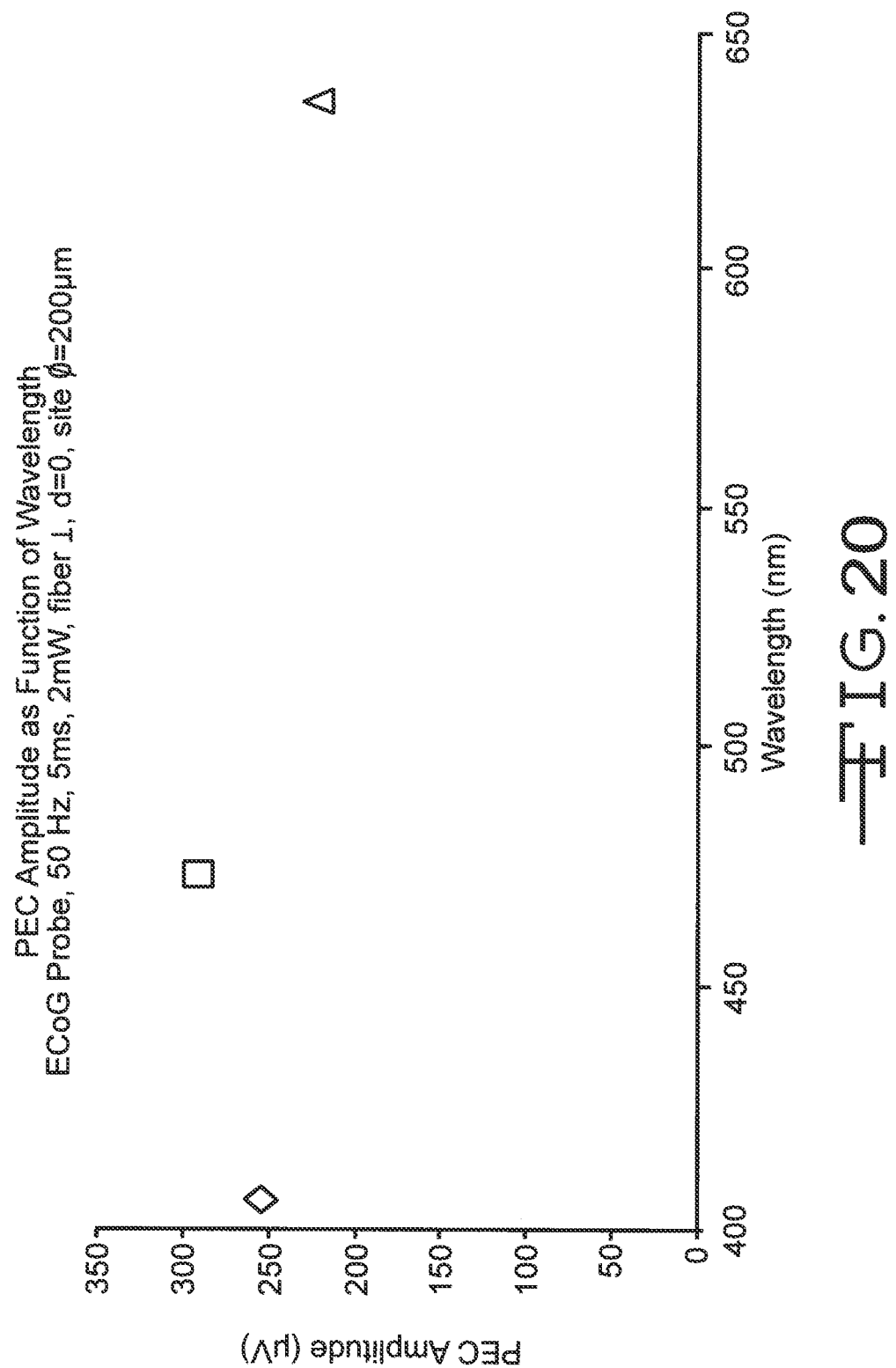
FIG. 20 is a graph of the sensitivity of the PEC effect to various wavelengths.

In one embodiment, the light irradiance on an electrode site is preferably at least about $1.5\,mW/mm^2$, but can alternatively be any suitable irradiance. It has been shown that a small PEC effect is detectable from the root-mean-square (RMS) noise even at a relatively low irradiance of about 0.3 mW/mm². Furthermore, in applications in which the test system 10 is measuring the continuity of multiple conductive paths from multiple electrical sites on a medical device, the light source 22 can irradiate different sites with different intensities. The light source 22 may include one or more of several light source types. Preferably the emitted light is in the visible spectrum. Additionally or alternatively, the light source can emit electromagnetic radiation in one or more wavelengths that are of an intensity that is sufficient to induce a PEC effect. As shown in FIG. 20, a range of wavelengths from about 400 nm to about 650 nm in the visible light spectrum can induce a PEC effect having measurable amplitudes. One preferred wavelength is 473 nm. For example, broadband white light from an LED has been shown to induce a PEC effect. Ultraviolet light through the visible spectrum is also acceptable.

Figure 17B:
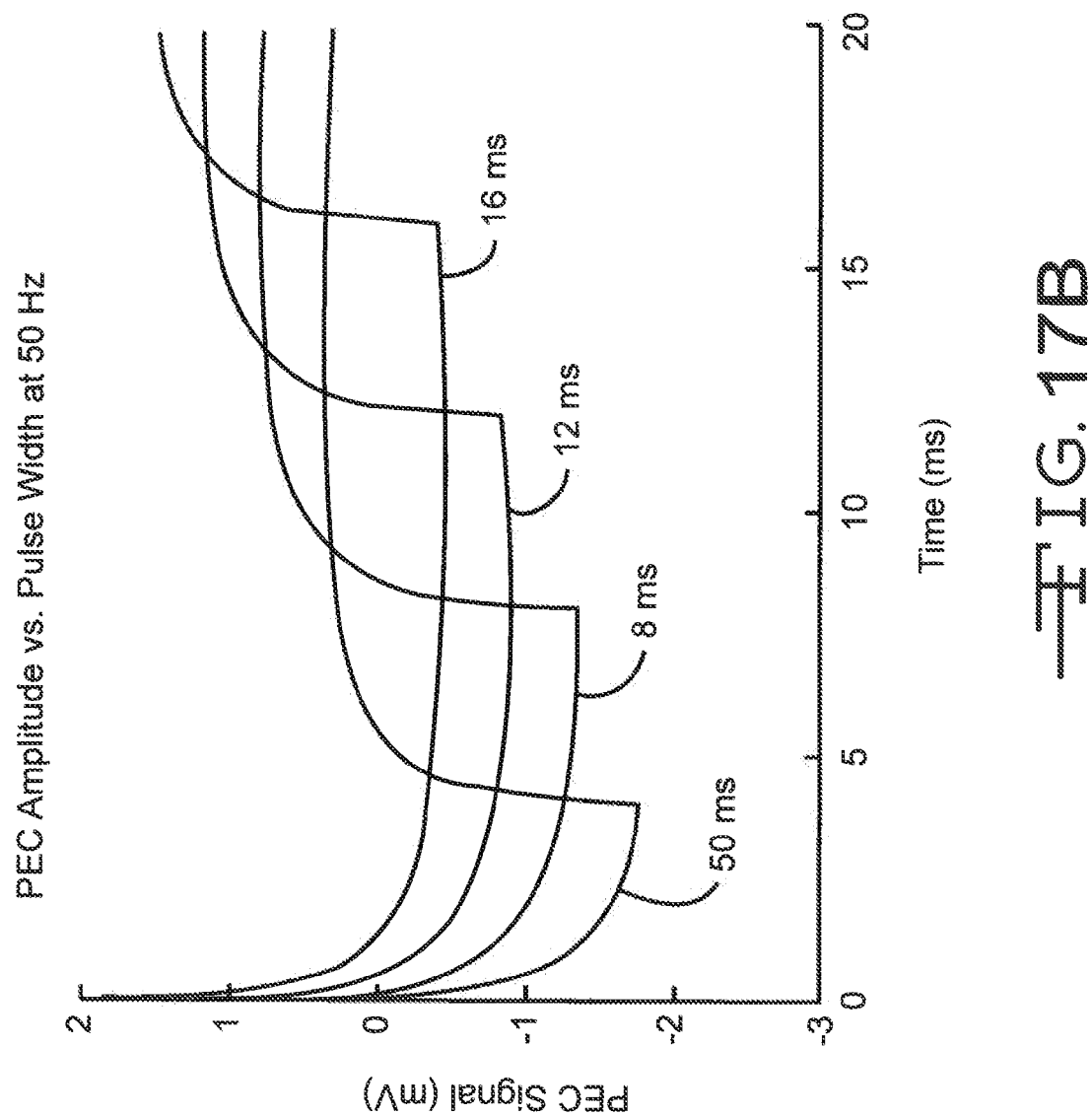
Figure 17C:
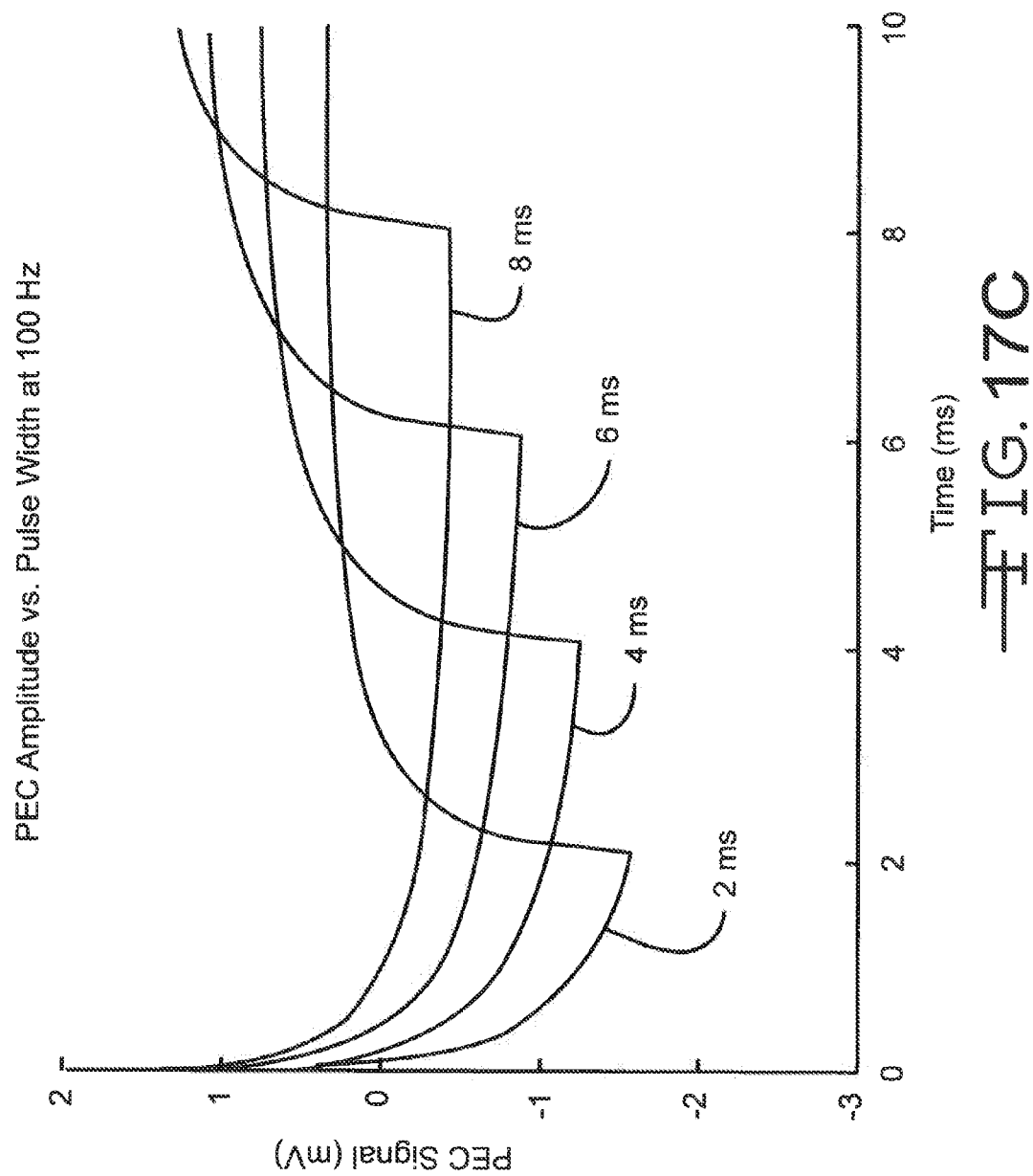
Figure 18:
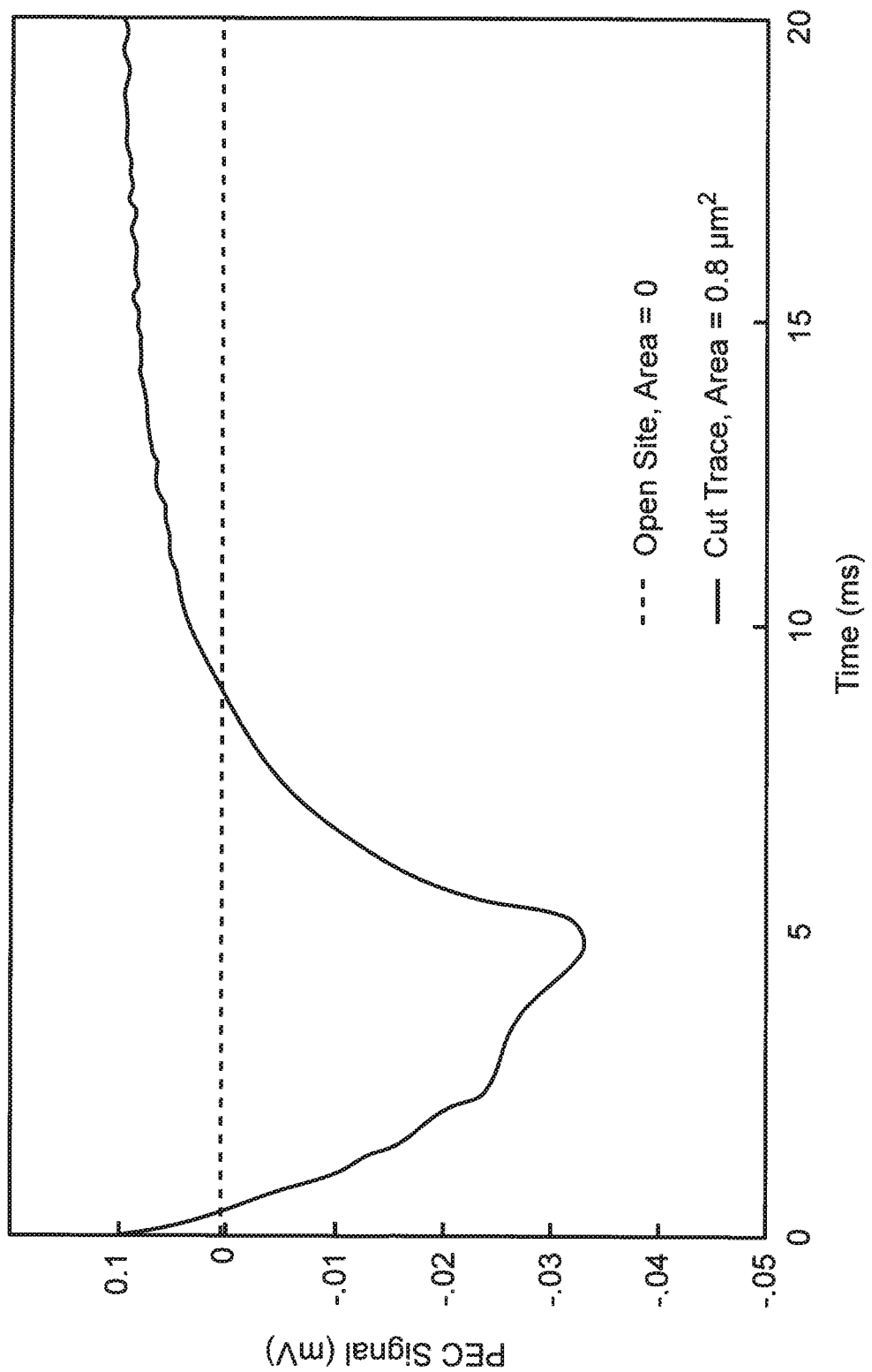
FIG. 18 shows the high sensitivity of the PEC effect on electrodes of sub-micron diameter.

The light source 22 can be modulated at various pulse widths. FIGS. 17A, 17B and 17C show the PEC signal at frequency of 10 Hz, 50 Hz, and 100 Hz, respectively, and duty cycles of 20%, 40%, 60%, and 80% at each of these frequencies. This illustrates the sensitivity of the PEC effect to various pulse widths. However, any suitable frequency and pulse width may be used.

In a first embodiment, the light source 22 is configured to emit light across a broad band of wavelengths. For example, the light source 22 can include a xenon lamp, halogen lamp, deuterium lamp, fluorescent lamp, or a white LED, such as a blue LED with a phosphorus coating. In a second embodiment, the light, source 22 is configured to emit light of a particular wavelength in narrow band of wavelengths. For example, the light source 22 can include a laser or LED of a specific wavelength.

In one embodiment, the detection system 26 is configured to detect and measure at least one of voltage or current at the second electrical site 28, such as a test pad or bond pad on the conductive path 12. In an electrical device in which the conductive path 12 is unbroken, the detected and measured voltage or current is the result of the PEC effect induced at the first electrical site 20, and is significantly higher than that measured in a device in which the conductive path 12 lacks electrical continuity or is open. The detection system 26 preferably includes at least one detection probe 36 and at least one detector 38. Alternatively, the detection system 26 includes multiple detection probes 36, 36A, each being contactable with a respective one of a multiplicity of electrical sites.

The detection probe 36 functions to detect an electrical signal, whether it is of a voltage potential or current, from the second electrical site 28 on the conductive path 12. The detection probe 132 is preferably configured to be in physical contact with the second site 28, such as a bond pad, that corresponds to the irradiated electrode. In one embodiment, the system 10 includes multiple detection probes 36, 36A that are each contactable to a respective bond pad or other electrical contact site. The multiple probes 36, 36A are configured to detect multiple electrical signals in parallel, or to sequentially detect a number of electrical signals in a serial arrangement without requiring repositioning of the probes 36, 36A. Detecting multiple signals in parallel is especially useful for identifying short-circuits.

Currently, the most convenient and cost-effective method to measure a short circuit is to sequentially measure impedance at a plurality of electrical sites and then flag any two or more sites having relatively equal magnitudes below an average magnitude. However, this technique can lack reliability when there are only two shorts, which is common, and the site-to-site impedance variance is relatively high. Alternatively, this invention may use multi-channel amplifiers for simultaneous measurements while illuminating one electrode site at a time. Because the electronics of the detection system 26 provide for simultaneous measurements, the PEG technique can accurately identify shorts.

As shown in FIG. 19A, shorted electrode sites 20 and 20A simultaneously display a PEG signal of approximately equal magnitude when only site 20A is illuminated (asterisk indicates illuminated site). When an electrically continuous site is illuminated, a PEC signal is displayed on only that electrical channel, unless the electrical, channel is capacitively, inductively, or resistively coupled to another electrical channel. As shown in FIG. 19B, the impedance measurement and the PEC effect provide similar information about shorts. The advantage of the PEC effect lies in the ease of simultaneous detection of shorts.

Figure 13A:
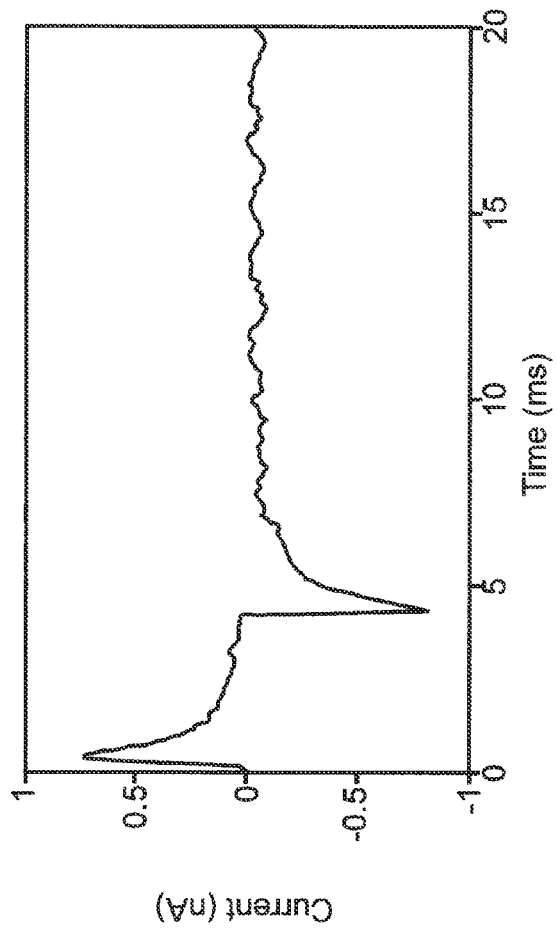
FIGS. 13A and 13B are graphs constructed from the PEC signal after illumination of the PEG terminal when using a galvanostat and a potentiostat, respectively.
Figure 13B:
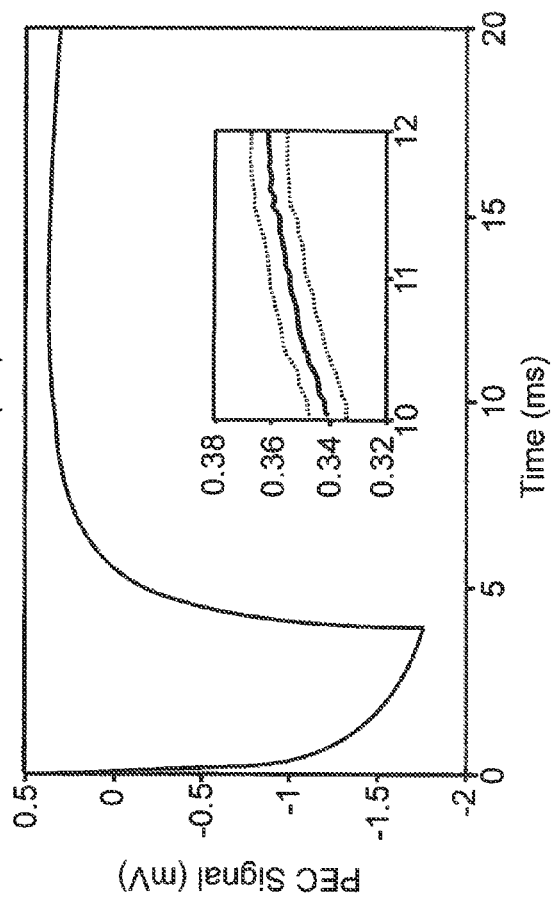

The detector 38 measures the electrical signal received by the probe 36. In particular, the detector 38 is preferably configured to measure the amplitude of the voltage or amount of current in the electrical signal resulting from the PEC event conveyed by the probe 36. FIGS. 13A and 13B, respectively, illustrate that current or voltage may be induced at the PECT or first electrical site 20 using an ammeter or amperometry system or a galvanostat, respectively. Detection of voltage can be accomplished using a high-impedance amplifier or potentiostat. In a broader sense, the detector 38 can include any general electronic components that use analog or digital electronics, for example an A/D converter.

As shown in FIG. 1, the detection system 26 preferably further includes a signal processor component 40. The signal processor component 40 preferably includes an amplifier that relays and amplifies the signal from the probe 36 to the detector 38. The signal processor 40 can further include components to reduce noise and thereby increase the signal-to-noise ratio.

In one embodiment, the test system 10 includes a central processor and software algorithm 42 that functions to evaluate the voltage and/or current measured at the second electrical site 28 on the conductive path 12. The central processor 42 compares the measured voltage or current at the second electrical signal 28 to a threshold, and is programmed to determine the electrical continuity or impedance equivalent of the conductive path 12 based on the comparison. In one embodiment, the central processor 42 compares the absolute value of the voltage or current in the electrical signal to a predetermined threshold. In another embodiment, the central processor 42 compares a relative change in voltage or current in the electrical signal, for example the change from a baseline measurement before inducing the PEC effect to a predetermined threshold.

As shown in FIG. 1, the central processor 42 can store data digitally and/or be coupled to an alert device 44 that visually or audibly indicates the presence of either a broken or unbroken electrical path, as the case may be. In another embodiment, the central processor 42 is coupled to a mechanical sorter on a manufacturing assembly line that automatically sorts devices that do not meet specifications for commercial acceptability and culls them for isolation, disposal, rework, or further inspection. Obviously, sorting may also occur at a later step if any electrical device fails and the failure has been digitally stored with a unique device identifier.

In all embodiments, the test system 10 includes a counter electrode channel 46 that provides a connection to the detection circuit, either as a common ground or a differential input signal compared with the input from the contact pad 36. As shown in FIG. 1, the counter electrode 46 uses the electrolyte 18 as a conductive medium to close the circuit. In this embodiment, the counter electrode channel 46 is a single channel electrode, such as a conductive microwire. The single channel electrode 46 may be supported by the fluidic channel or probe 16, or any other suitable component of the test system 10. Preferably the counter electrode is connected at a distant location on the contiguously pattern electrolyte medium while still forming a completed electrical circuit.

As shown in FIG. 2, the test system 10 further includes a controller 48 that coordinates movement or repositioning of at least the light source 22 or the probe 36. The optional fluidic channel 16 and counter electrode 46 may also be controlled to move with the light source, but preferably the electrolyte is patterned prior to the testing phase and thus the fluidic channel and counter electrode are not required to move. The controller 48 can also coordinate movement of the medical device 14 relative to the system 10. The controller 48 can be implemented on any suitable computing device.

In a first preferred embodiment, the controller 48 provides fully automated or semi-automated testing. For example, the system 10 can receive one or more medical devices 14 fed in serial or parallel fashion on an automated assembly line. The controller 48 is programmed with mapped coordinates 50 of the medical device and relevant conductive paths such as specific electrical sites or bond pads. The controller 48 is programmed to move the fluidic channel 16, light source 22, probe 36, or counter electrode channel 46 relative to the mapped coordinates 50 to provide signal measurements of one or a plurality of conductive paths 12 in an automated fashion. That would be to match electrical signal measurements to corresponding conductive paths 12. Additionally, the controller 48 is programmed to move the medical device 14 relative to the reference positions of the fluidic channel 16, light source 22, probe 36, or counter electrode channel 46. The controller 48 enables testing of multiple conductive paths 12 on a medical device in a serial manner, such as by methodically controlling the system 10 to induce a PEG effect on different electrical sites 20, 20A to 20C in scanning- or raster-like fashion.

In another embodiment, the controller 48 is programmed to allow manual testing. In that manner, an operator can manually position the light source 22, probe 36, or counter electrode channel 46 relative to the medical device 14 as desired for testing a particular conductive path 12.

Alternative Embodiment of the System

In an alternative embodiment of the test system 10, the microfluidic dispenser 16 and electrolyte 18 are eliminated. Instead, a thin film of gel, such as a hydrogel, photoresist or other transparent or semi-transparent organic medium is patterned onto the wafer or electronic device 14 prior to testing. The gel comprises one of the electrolytes listed in FIG. 16A, such as KOH, a fluid such as deionized water and, optionally, a humectant to ensure hydration over a desired time period. The resulting gel should be from about 10 µm to about 1,000 µm thick and be at least as conductive as 0.0001 M KOH. This gel film is at least semi-transparent (allows passage of light from the light source 22) and contains ions, acids, and/or bases such that the formed surface species create a photoelectrochemical event for the light wavelength being used. The gel film preferably has sufficient conductivity such that any thermal noise in the test circuit does not dominate the photoelectrochemical artifact.

In one embodiment, the gel film includes 0.05% of dry AgCl (weight/volume) mixed with a suitable photoresist. The gel film can be deposited, patterned, exposed, and developed using any suitable thin film technique, such as inkjet technology. This alternative embodiment of the test system 10 can be used, for example, in applications in which one or more electronic devices 14 have varying relative positions between the first electrical site 20 and the second test pad 28. In another embodiment, the gel film is directly written using a programmable inkjet array having been loaded with a slightly basic solution, e.g. 0.005 KOH, or other suitable ionic species and having a viscosity compatible with the inkjet dispenser.

Although omitted for clarity, the preferred embodiments of the test system 10 include every combination of the variations of the fluidic channel 16, light source 22, detection system 26, central processor 42, counter electrode channel 46, controller 48, and other components described hereinabove.

Figure 15:
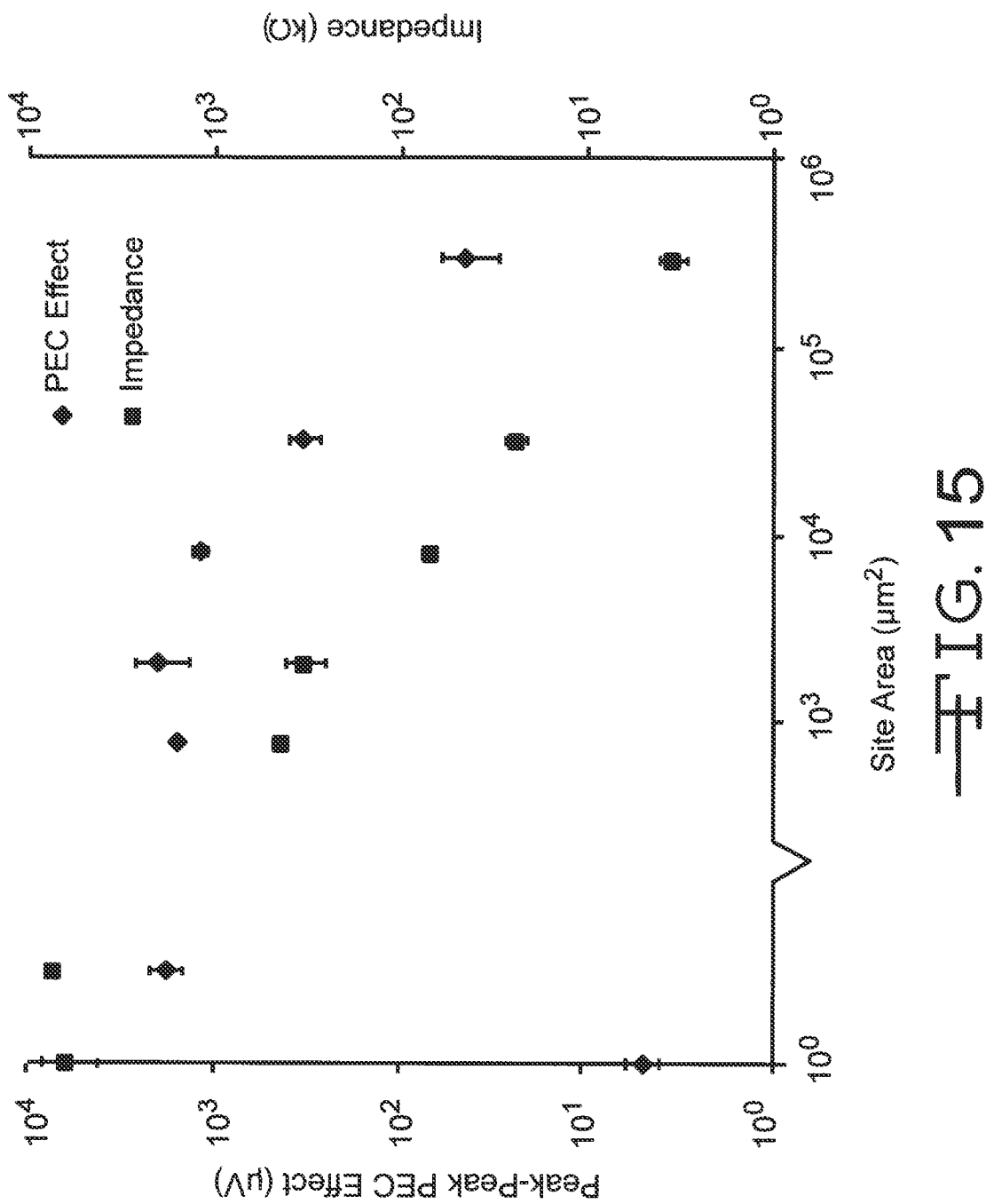
FIG. 15 is a chart comparing the sensitivity of impedance measurements and PEG measurements as a function of electrode or PECT area.

In addition to testing circuit continuity in a passive circuit, the induced current and/or voltage at the PECT or first site 20 can be used to measure the electrode or bond pad surface area. Both electrical impedance and PEC measurements are electrochemical phenomena inversely proportion to the electrode area over a range of area values. Thus, in order to measure area using the PEC effect, one only needs to measure the PEC amplitude as a function of controlled areas a priori for a given set of parameters. The graph shown in FIG. 15 was constructed from a PEG test using a light pulsed at 50 Hz, 25% duty cycle, and 1 mW power output. The graphed sensitivity and detection limits where created with the fiber optic light positioned 1 mm above a platinum electrode. With any platinum electrode the indicated sensitivity range will correlate the measured voltage amplitude to a given surface area.

Figure 5:
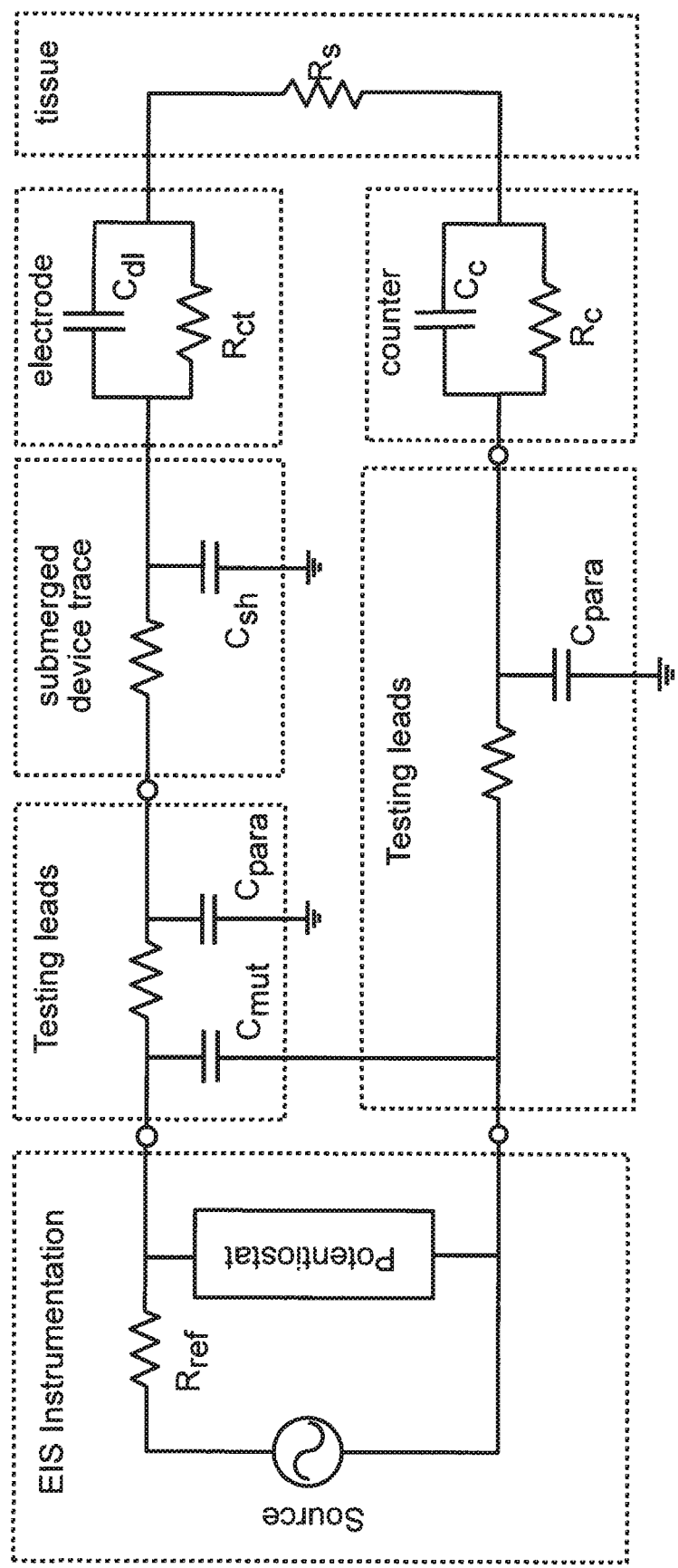
FIG. 5 illustrates the prior art of electrical impedance spectroscopy.

Impedance spectroscopy lacks sensitivity for detecting open circuits when measuring very small electrodes (contact pads in an electrolyte) if the measuring circuit requires a multiplexer or long leads or several connections. FIG. 5 illustrates an equivalent circuit model for an impedance measurement system according to the prior art. Notice that if the conductive trace 12 is an open-circuit then the signal generated at the source may still complete the circuit by traveling through the parasitic capacitance and specifically through the mutual capacitance (Cmut) and shunt capacitance (Csh).

Figure 6:
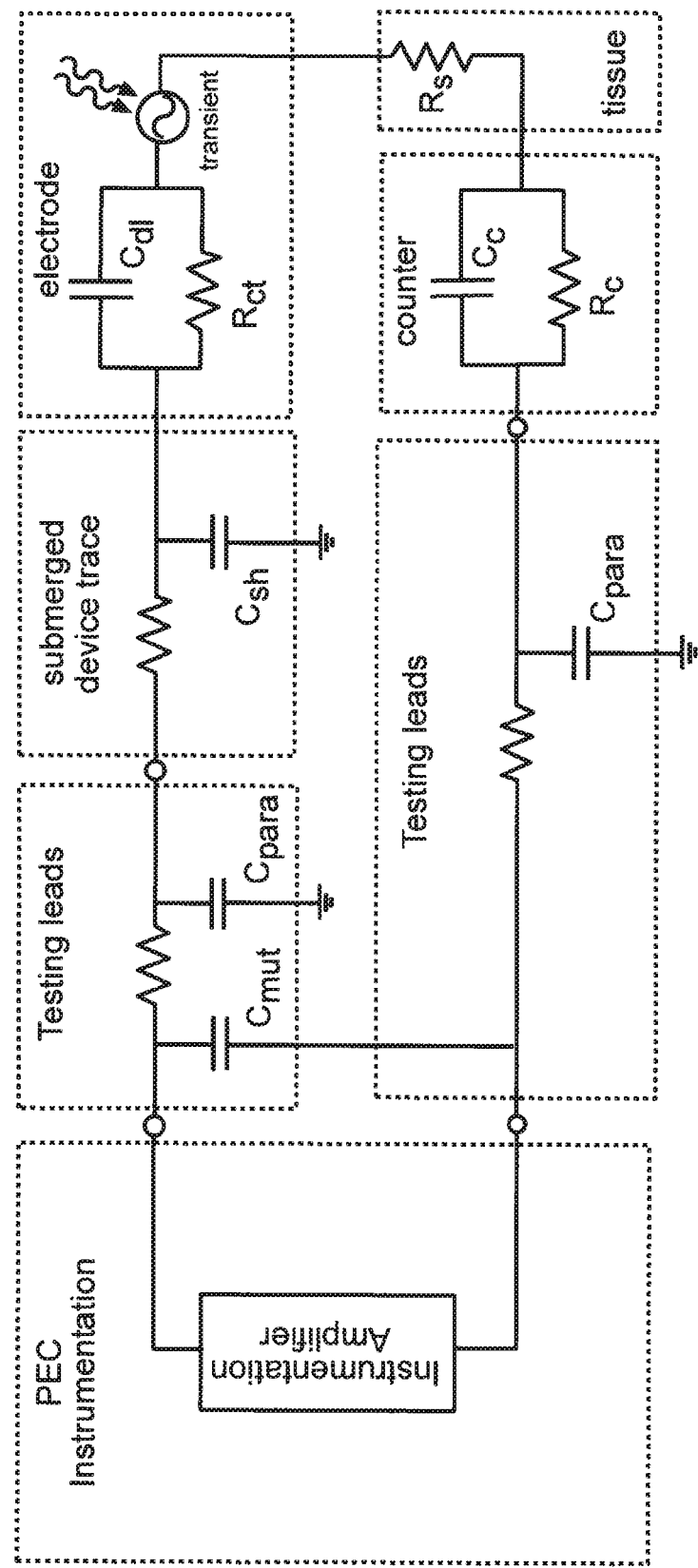
FIG. 6 illustrates the equivalent circuit of a PEG measurement system according to the present invention.

By contrast, the PEG effect is highly sensitive to open-circuit failures for electrodes or bond pads much smaller than impedance can detect. FIG. 6 illustrates this in a similar equivalent circuit according to the present invention. Notice the primary difference with the prior art circuit of FIG. 5 is that the location of the source signal is such that an open circuit in the conductive trace 12 prevents the signal from reaching the testing leads and greatly reduces the signal being coupled capacitively. In that respect, the present invention has been used to detect closed and open circuits in electrodes as small as 400 nm by 2000 nm.

Figure 3B:
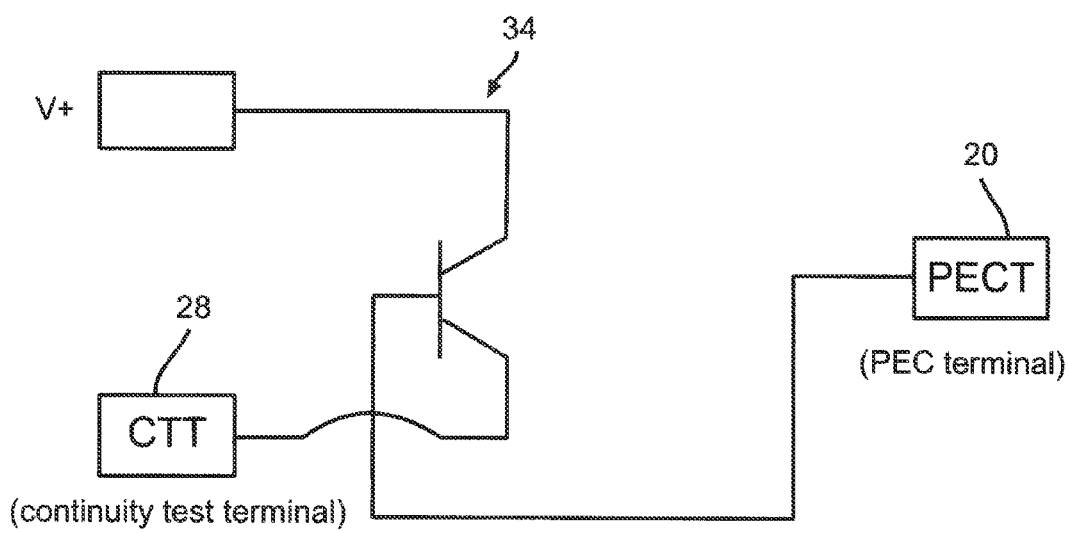

If the surface area is known, then the PEG effect can be employed to measure other circuit components such as transistor function. This additional function requires the ability to control the induced voltage and/or current at the PECT or first site 20 (FIG. 3B). A range of voltage and current may be induced in the circuit by varying the irradiance (FIG. 14), electrode or PECT area (FIG. 15), electrolyte pH (FIG. 16), pulse width (FIG. 17), and wavelength (FIG. 20). Thus, the present method described herein can be used to test low-voltage transistor terminals (or other IC related circuits) provided the induced voltage and current at the PECT or first electrical site 20 is controlled. Low-voltage transistors (e.g., tunneling field effect transistor) could especially benefit from the PEC effect as a probing mechanism since very small terminals would reduce the area of the chip or circuit.

Detecting short-circuits and capacitive connections in circuits and electrodes have also been demonstrated (FIGS. 11 and 19). A PEC measurement system capable of short-circuit detection requires multiple voltage detectors. The high impedance amplifiers required for this are low-cost and easily scalable.

Figure 7:
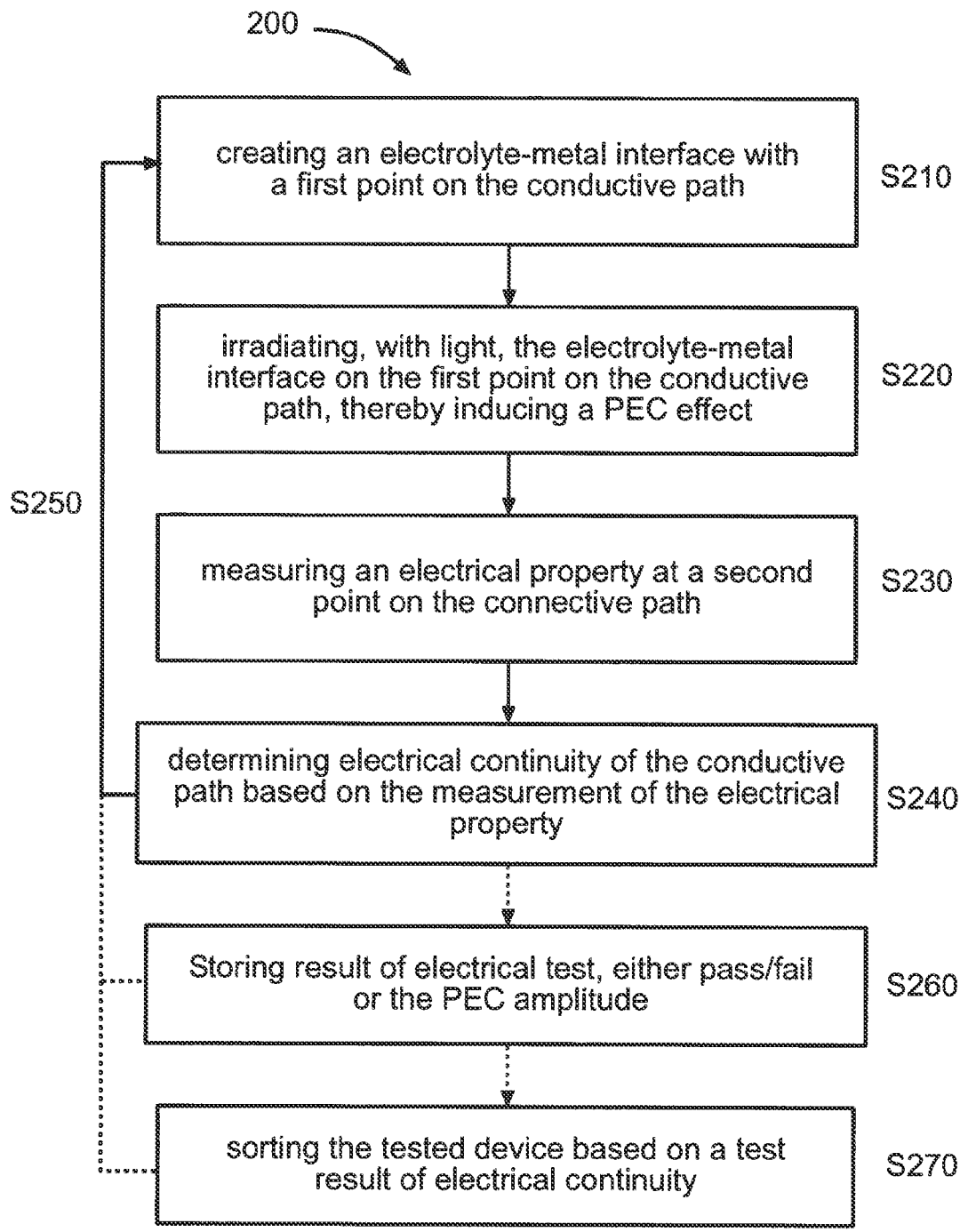
FIGS. 7 to 10 are flowcharts of various methods for practicing the present invention.

Method for Testing Electrical Continuity Including the Electrode-Electrolyte Impedance Equivalent FIG. 7 is a flow diagram for a method 200 of testing the electrical continuity or impedance equivalent of a conductive path 12 on an electronic device 14 according to the present invention. In block S210, an electrode-electrolyte interface 24 is created at a first electronic point or site 20 on the conductive path 12. In block S220, a light source 22 is used to irradiate the electrode-electrolyte interface 24 on the first electronic site 20, thereby inducing a photoelectrochemical (PEC) effect at the site. Block S220 can include irradiating the electrode-electrolyte interface 24 with a broadband spectrum of light 38', or a single (or relatively narrow) wavelength of light 38, at any suitable frequency and at any suitable intensity.

In block S230, an electrical property is measured at a second electrical point or site 28 on the conductive path 12. In block S240, the presence or lack of electrical continuity in the conductive path 12 is based on measurement of the electrical property. The PEC effect preferably produces a change in the voltage and/or current in an unbroken conductive path 12 from the first electronic site 20 to the second site 28. Measurement of voltage and/or current at the second site 28 is then used to determine whether there is electrical continuity or discontinuity with the first electronic site 20 where the PEC effect is induced. In a device 14 in which the conductive path 12 is unbroken, the detected and measured voltage or current is significantly higher than that measured in a device in which the conductive path is open.

For clarity, the preferred method 200 is primarily described herein in reference to a first electrical point or site 20 where the PEG effect is induced and a second site 28 on the conductive path 12 where a voltage or current is measured. The first site can be an electrode on the conductive path 12 of a medical device while the second site 28 is a bond pad at the proximal end of the medical device. However, it should be understood that the preferred method can be configured to test for continuity or discontinuity between any two suitable point or sites on a conductive path of a medical device or of any suitable device.

Figure 8:
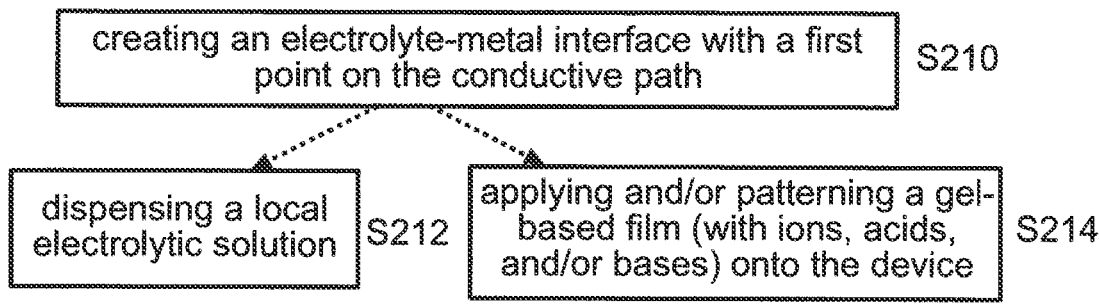

In an alternate embodiment shown in FIG. 8, the method 200 further includes block S212, which recites dispensing an electrolyte from a fluidic channel 16 onto the first electrical point or site 20 of the conductive path 12. The electrolyte can also be dispensed on each of a plurality of individual electrical sites 20, 20A to 20C in series. For instance, the electrolyte dispenser 16 can be moved between electrodes 20, 20A to 20C in series, and/or the medical device 14 can be physically moved to serially align each of multiple electrical sites 20, 20A to 20C with the electrolyte dispenser 16. The method 200 also contemplates dispensing the electrolyte 18 onto multiple electrical sites 20, 20A to 20C arranged in a parallel alignment.

In an alternative method shown in FIG. 8, block S214 recites applying and/or patterning a film onto the device 14. The film is preferably a thin film of gel, photoresist, or other transparent or semi-transparent organic medium that can be patterned onto the device 14 being tested. The film is preferably at least semi-transparent to allow passage of the light 38, 38' from the light source 22 onto the electrical site 20. The film preferably includes ions, acids, and/or bases such that the formed surface species creates a PEC event with the incident light wavelength(s). The film preferably has sufficient conductivity such that the thermal noise in the test circuit does not dominate the photoelectrochemical artifact.

In one embodiment, the film includes 0.05% of dry AgCl (weight/volume) mixed with a suitable photoresist. The film can be deposited, patterned, exposed, and developed in any suitable thin film techniques. This alternative embodiment of the method can be used, for example, in applications in which the one or more devices 14 being tested have varying relative positions between their test pad 28 and the electrical site 20.

Figure 9:
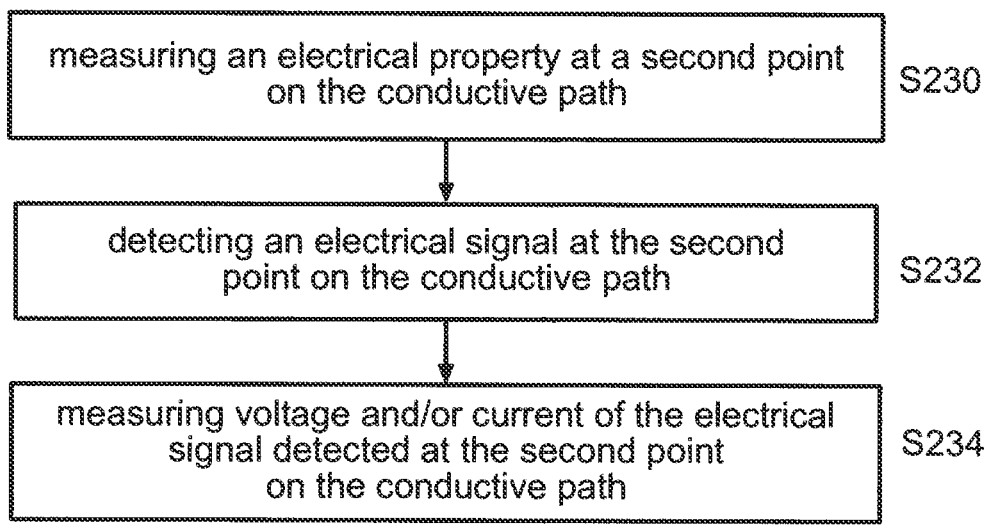

As shown in FIG. 7, block S230 recites measuring an electrical property at a second electrical point or site 28 on the conductive path 12. In that manner, block S230 functions to obtain data that can be used to determine electrical continuity or impedance equivalent between the first electrical site 20 (e.g., electrode) and the second electrical site 20 (e.g., bond pad) on the conductive path 12. As shown in a preferred embodiment depicted in FIG. 9, the method 200 includes detecting an electrical signal at the second site 28 in block S232, and measuring the voltage or current of the electrical signal in block S234. Block S232 preferably includes detecting the electrical signal at the second electrical point or site 28 with a probe 36 in physical contact therewith. The preferred method 200 can additionally or alternatively include measuring any suitable electrical property of the detected electrical signal. In one variation, the method 200 preferably further includes amplifying the detected signal, reducing noise of the detected signal, and/or performing any suitable signal processing steps.

Figure 10:
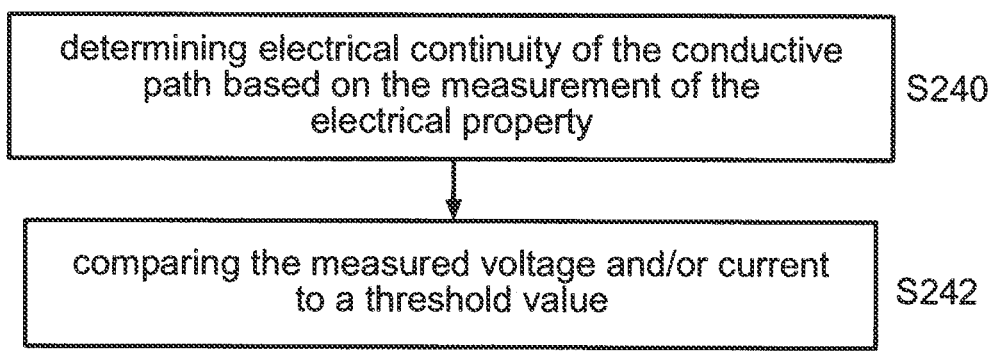

As shown in FIG. 7, block S240 recites determining electrical continuity or impedance equivalent of the conductive path based on the measurement of the electrical property. Block S240 preferably functions to evaluate the measurement of the electrical property to produce a result of whether there is electrical continuity along the conductive path 12, or not. In block S242 of FIG. 10, a determination of electrical continuity includes comparing the measured voltage or current to a threshold value. That includes comparing the absolute value of the voltage or current in the electrical signal to a predetermined threshold. In another variation, a relative change in voltage or current in the electrical signal (e.g., change from a baseline measurement in voltage or current in the electrical signal) is compared to a predetermined threshold.

As shown in FIG. 7, the preferred method 200 includes block S260, which recites alerting an operator of a failed test result. For example, in a test for electrical continuity or impedance equivalent, the method 200 can alert the operator in the event a conductive path 12 is determined to be broken (open circuit). As another example where the test is for a desirable open circuit, the method can alert the operator in the event of an unwanted electrical continuity along the conductive path 12. The alert 44 may be made in a visual manner using lights or text on a user interface, aural using a device that produces a buzz or beep, or in any other suitable manner. The preferred method 200 can include mapping 50 the variously tested conductive paths, such as on a schematic image of the device, and indicating respective electrical continuity and discontinuity of each conductive path, as determined by the test method.

Block S270 in FIG. 7 depicts sorting the tested device 14 based on a test result of electrical continuity or discontinuity, as determined by the test method. For example, in an application in which the preferred method 200 is performed by an automated manufacturing assembly line, the preferred method 200 can include sorting failed devices from passed devices for isolation, disposal, rework, and/or further inspection.

In another variation of the method of the present invention, at least blocks S210 through S240 are repeated along arrow S250. Arrow S250 relates to repeating each of blocks S210 through S240, either in a serial or parallel manner. That can be done for multiple conductive paths on a single electronic device 14. Blocks S260 and/or S270 can additionally be repeated. In some embodiments, the present method 200 can further be repeated for multiple devices, such as on an automated assembly line.

Example

The following exemplary implementation of the present system and method is for illustrative purposes only, and should not be construed as definitive or limiting of the scope of the invention.

A neural interface probe with twelve channels or conductive paths between respective pairs of electrical site or test pads was tested for electrical continuity or impedance equivalent along the channels using the present testing system. A microfluidic channel was used to dispense a few microliters of electrolyte onto each electrical contact of the neural probe. An optical fiber configured to emit 5 ms pulses of light having a wavelength of 473 nm, a frequency of 50 Hz, and intensity of 2 mW was used as a light source. The detection system included multiple detector probes, each in contact with a respective electrical site or test pad. A voltage amplitude measurement was taken at the test pad.

The optical fiber emitted a focused beam of light approximately perpendicular to the electrical site from a distance of approximately zero. In other words, the optical fiber was touching, or nearly touching, the first electrical site. As shown in the graph of FIG. 11, as the various electrodes or electrical sites of the neural interface probe were sequentially illuminated, the detection system sensed and recorded a significantly higher voltage for a respective test site corresponding to an illuminated electrode than for the other test sites that were not being illuminated. In other words, as this data in strongly suggests, the system detects significantly higher voltage artifact amplitude along each channel in which the PEG effect is induced, suggesting that all three channels in the particular neural interface probe being tested were intact and possessed electrical continuity.

Moreover, as shown in FIG. 11, the adjacent site to the illuminated site displays a higher PEG amplitude than a distant site, which was located approximately 900 μm from the illuminated site 20. This is due to capacitive coupling of the signal caused by the proximity of the electrical paths of the illuminated and adjacent sites.

As a person skilled in the art will recognize from the previous detailed description and from the figures and claims, modifications and changes can be made to the preferred embodiments of the invention without departing from the scope of the invention defined in the following claims.

What is claimed is:

1. A method for determining the electrical continuity of a conductive trace, comprising the steps of:
   a) providing an electronic device comprising an electrically conductive trace having a length extending from at least a first electrical site spaced from a second electrical site;
   b) contacting an electrolyte to the first electrical site along the conductive trace;
   c) irradiating the electrolyte contacting the first electrical site with a light source, thereby inducing a photoelectrochemical (PEC) effect at the interface between the electrolyte and the first electrical site;
   d) contacting an electrical probe to the second electrical site along the conductive trace,
   e) wherein the electrical probe is configured to measure at least one of an electrical potential and current at the second electrical site as a result of the PEG effect at the first electrical site.

2. The method of claim 1 including providing the electronic device having the conductive trace supported on an insulative substrate.

3. The method of claim 1 including determining from the measured at least one of the electrical potential and the current that the conductive trace is either continuous or discontinuous from the first electrical site to the second electrical site.

4. The method of claim 1 including providing the conductive trace of a material selected from the group consisting of gold, platinum, iridium, tungsten, platinum-iridium, PEDOT, iridium oxide, doped diamond, graphite, carbon nanofiber, poly(3,4-ethylenedioxythiophene), and combinations thereof.

5. The method of claim 1 including selecting the electrolyte from the group consisting of HCl ranging from about 0.01M to about 0.005M, KOH ranging from about 0.0001M to about 0.1M, deionized water, phosphorous buffered saline, and mixtures thereof.

6. The method of claim 1 including providing the electrolyte as a liquid medium.

7. The method of claim 1 including providing the electrolyte as a gel-like medium.

8. The method of claim 1 including providing the gel electrolyte containing at least one of the group consisting of polyethylene glycol, glycerine, and carboxymethylcellulose.

9. The method of claim 1 including providing the light source configured to irradiate the interface between the electrolyte and the first electrical site with an irradiance ranging from about 0.3 mw/mm$^2$ to about 1.5 mw/mm$^2$.

10. The method of claim 1 including selecting the light source from the groups consisting of a xenon lamp, a halogen lamp, a deuterium lamp, a fluorescent lamp, a white LED and a blue LED with a phosphorous coating.

11. The method of claim 1 including illuminating the interface between the electrolyte and the first electrical site with a wavelength ranging from about 400 nm to about 650 nm.

12. The method of claim 1 including providing the conductive trace comprising platinum with a surface area of the first electrical site being inversely proportional to an electrical impedance measurement derived from the PEC effect.

13. A method for determining the electrical continuity of a conductive trace, comprising the steps of:
   a) providing an electronic device comprising an electrically conductive trace having a length extending from at least a first electrical site spaced from a second electrical site;
   b) contacting an electrolyte to both the first and second electrical sites;
   c) irradiating the electrolyte contacting the first electrical, site with a light source, thereby inducing a photoelectrochemical (PEC) effect at the interface between the electrolyte and the first electrical site;
   d) contacting an electrical probe to the second electrical site along the conductive trace,
   e) wherein the electrical probe is configured to measure at least one of an electrical potential and current at the second electrical site as a result of the PEG effect at the first electrical site.

14. The method of claim 13 including providing the electronic device having the conductive trace supported on an insulative substrate.

15. The method of claim 13 including determining from the measured at least one of the electrical potential and the current that the conductive trace is either continuous or discontinuous from the first electrical site to the second electrical site.

16. The method of claim 13 including providing the conductive trace of a material selected from the group consisting of gold, platinum, iridium, tungsten, platinum-iridium, PEDOT, iridium oxide, doped diamond, graphite, carbon nanofiber, poly(3,4-ethylenedioxythiophene), and combinations thereof.

17. The method of claim 13 including selecting the electrolyte from the group consisting of HCl ranging from about 0.01M to about 0.005M, KOH ranging from about 0.0001M to about 0.1M, deionized water, phosphorous buffered saline, and mixtures thereof.

18. The method of claim 13 including providing the electrolyte as a liquid medium.

19. The method of claim 13 including providing the electrolyte as a gel-like medium containing at least one of the group consisting of polyethylene glycol, glycerine, and carboxymethylcellulose.

20. The method of claim 13 including providing the light source configured to irradiate the interface between the electrolyte and the first electrical site with an irradiance ranging from about 0.3 mw/mm$^2$ to about 1.5 mw/mm$^2$.

21. The method of claim 13 including illuminating the interface between the electrolyte and the first electrical site with the light source having a frequency ranging from about 10 Hz to about 100 Hz.

* * * * *